US007003403B1

(12) United States Patent
Dougherty et al.

(10) Patent No.: US 7,003,403 B1
(45) Date of Patent: Feb. 21, 2006

(54) QUANTIFYING GENE RELATEDNESS VIA NONLINEAR PREDICTION OF GENE

(75) Inventors: Edward R. Dougherty, College Station, TX (US); Seungchan Kim, College Station, TX (US); Michael L. Bittner, Rockville, MD (US); Yidong Chen, Rockville, MD (US)

(73) Assignees: The United States of America as represented by the Department of Health and Human Services, Washington, DC (US); The Texas A & M University System, College Station, TX (US)

( * ) Notice: Subject to any disclaimer, the term of this patent is extended or adjusted under 35 U.S.C. 154(b) by 649 days.

(21) Appl. No.: 09/595,580

(22) Filed: Jun. 15, 2000

(51) Int. Cl.
*G01N 33/48* (2006.01)
*G06G 7/00* (2006.01)
*C12Q 1/68* (2006.01)

(52) U.S. Cl. .................. 702/19; 702/20; 706/15; 706/21; 435/6

(58) Field of Classification Search ............... 435/6; 364/496; 702/19, 20; 706/15, 21
See application file for complete search history.

(56) References Cited

U.S. PATENT DOCUMENTS

| 5,519,496 | A |   | 5/1996 | Borgert et al. |
| 5,526,281 | A | * | 6/1996 | Chapman et al. ........... 364/496 |
| 5,557,734 | A |   | 9/1996 | Wilson |
| 5,708,591 | A |   | 1/1998 | Givens et al. |
| 5,769,074 | A | * | 6/1998 | Barnhill et al. ............ 128/630 |
| 5,968,784 | A |   | 10/1999 | Spinella et al. |
| 6,023,530 | A |   | 2/2000 | Wilson |
| 6,025,128 | A |   | 2/2000 | Veltri et al. |
| 6,040,138 | A |   | 3/2000 | Lockhart et al. |
| 6,059,561 | A |   | 5/2000 | Becker |
| 6,132,969 | A | * | 10/2000 | Stoughton et al. .......... 435/6 |
| 2003/0152969 | A1 |   | 8/2003 | Quake et al. |

FOREIGN PATENT DOCUMENTS

| WO | WO 99/44062 | 9/1999 |
| WO | WO 99/44063 | 9/1999 |
| WO | WO 00/50643 | 8/2000 |

OTHER PUBLICATIONS

Jian et al. (IEEE Transacations on Pattern Analysis and Machine Intelligence (2000) vol. 22:4-37.*
Chen et al., *Proc SPIE*, "Clustering Analysis for Gene Expression Data," vol. 3602:422-8, 1999.
Winston, *Artificial Intelligence*, "Learning by Training Perceptrons," Third Edition, Addison-Wesley Publishing Company, 1992.
U.S. Appl. No. 09/407,021, filed Sep. 28, 1999, Chen et al.
Dougherty et al., "Logical Image Operators," *Nonlinear Filters for Image Processing*, pp. 1-60, 1999.

(Continued)

*Primary Examiner*—Marjorie A. Moran
*Assistant Examiner*—Lori A. Clow
(74) *Attorney, Agent, or Firm*—Klarquist Sparkman, LLP

(57) ABSTRACT

Relatedness between genes is quantified by constructing nonlinear models predicting gene expression. Effectiveness of the model is evaluated to provide a measurement of the relatedness of genes associated with the model. Various types of models, including full-logic or neural networks can be constructed. A graphical user interface presents results of the analysis to allow evaluation by a user. Each gene's contribution to the measurement of relatedness can be shown on a graph, and graphical representations of models used to predict gene expression can be displayed.

81 Claims, 27 Drawing Sheets

OTHER PUBLICATIONS

Dougherty, "Efficient Design Strategies for the Optimal Binary Digital Morphological Filter: Probabilities, Constraints, and Structuring-Element Libraries," *Mathematical Morphology in Image Processing*, pp. 43-92, 1992.

Barrera et al., "Automatic Programming of Binary Morphological Machines by Design of Statistically Optimal Operators in the Context of Computational Learning Theory," *Journal of Electronic Imaging*, vol. 6, No. 1, pp. 54-67, Jan. 1997.

Salembier, "Structuring Element Adaptation for Morphological Filter," *Journal of Visual Communication and Image Representation*, vol. 3, No. 2, Jun., pp. 115-136, 1992.

Sarca et al., "Secondarily Constrained Boolean Filters," *Signal Processing*, vol. 71, pp. 247-263, 1998.

Barrera et al., "Hybrid Human-Machine Binary Morphological Operator Design. An Independent Constraint Approach," *Signal Processing*, vol. 80, pp. 1469-1487, 2000.

Grigoryan et al., "Design and Analysis of Robust Binary Filters in the Context of a Prior Distribution for the States of Nature," *Journal of Mathematical Imaging and Vision*, vol. 11, pp. 239-254, 1999.

Hirata et al., "A Switching Algorithm for Design of Optimal Increasing Binary Filters Over Large Windows," *Pattern Recognition*, vol. 33, pp. 1059-1081, 2000.

Dougherty et al., "Optimal Binary Differencing Filters: Design, Logic Complexity, Precision Analysis, and Application to Digital Document Processing," *Journal of Electronic Imaging*, vol. 5, No. 1, pp. 66-86, Jan. 1996.

Dougherty et al., "Optimal Iterative Increasing Binary Morphological Filters," *Optical Engineering*, vol. 35, No. 12, pp. 3495-3507, Dec. 1996.

Dougherty et al., "Precision of Morphological-Representation Estimators for Translation-Invariant Binary Filters: Increasing and Nonincreasing," *Signal Processing*, vol. 40, pp. 129-154, 1994.

Handley et al., "Model-Based Optimal Restoration of Fax Images in the Context of Mathematical Morphology," *Journal of Electron Imaging*, vol. 3, No. 2, pp. 182-189, Apr. 1994.

Dougherty et al., "Optimal Mean-Absolute-Error Hit-or-Miss Filters: Morphological Representation and Estimation of the Binary Conditional Expectaion," *Optical Engineering*, vol. 32, No. 4, pp. 815-827, Apr. 1993.

Loce et al., "Facilitation of Optimal Binary Morphological Filter Design via Structuring Element Libraries and Design Constraints," *Optical Engineering*, vol. 31, No. 5, pp. 1008-1025, May 1992.

Loce et al., "Optimal Morphological Restoration: The Morphological Filter Mean-Absolute-Error Theorem," *Journal of Visual Communication and Image Representation*, vol. 3, No. 4, pp. 412-432, Dec. 1992.

Dougherty, "Optimal Mean-Square N-Observation Digital Morphological Filters, I. Optimal Binary Filters," *CVGIP: Image Understanding*, vol. 55, No. 1, pp. 36-54, Jan. 1992.

Dougherty, "Optimal Mean-Square N-Observation Digital Morphological Filters, II. Optimal Gray-Scale Filters," *CVGIP: Image Understanding*, vol. 55, No. 1, pp. 55-72, Jan. 1992.

Wilson, "Training Structuring Elements in Morphological Networks," *Mathematical Morphology in Image Processing*, (Dougherty, ed.), pp. 1-41, 1993.

Kauffman, "Self-Organization and Adaptation in Complex Systems," *The Origins of Order*, pp. 173-235, 1993.

Chen et al.,*Proc SPIE*, "Clustering Analysis for Gene Expression Data," vol. 3602, pp. 422-428, 1999.

Winston, *Artificial Intelligence*, "Learning by Training Perceptrons," Third Edition, Addison-Wesley Publishing Company, pp. 471-489, 1992.

U.S. Appl. No. 09/407,201, filed Sep. 1999, Chen et al.

Michaels et al., "Cluster Analysis and Data Visualization of Large-Scale Gene Expression Data," *Pacific Symposium on Biocomputing* vol. 3, pp. 42-53, 1998.

Liang, "Reveal, A General Reverse Engineering Algorithm for Inference of Genetic. Network Architectures," *Pacific Symposium on Biocomputing* vol. 3, pp. 18-29, 1998.

Zhang et al., "Synthesis of Sigma-Pi Neural Networks by the Breeder Genetic Programming," *Proc. of Int. Conf. on Evolutionary Computation*, IEEE, pp. 318-323, 1994.

Frenkel, "The Human Genome Project and Informatics," *Communications of the ACM*, vol. 34, No. 11, Nov. 1991.

Manly, *Multivariate Statistical Methods*, Chapman and Hall Ltd., pp. 1-109, 1986.

Dougherty, *Random Processes for Image and Signal Processing*, SPIE Optical Engineering Press, pp. 451-481, 1999.

Dougherty (ed.) *Nonlinear Filters for Image Processing*, SPIE Optical Engineering Press, pp. 61-98, 1999.

Buhler, "Anatomy of a Comparative Gene Expression Study," http://www.cs.washington.edu/homes/jbuhler/research/array/, pp. 1-8, last update Mar. 24, 2000.

Chen et al., "Ratio-Based Decisions and the Quantitative Analysis of cDNA Microarray Images," *J. Biomed. Optics* vol. 2, pp. 364-374, Oct. 1997.

D'haeseleer et al., "Mining the Gene Expression Matrix: Inferring Gene Relationships from Large Scale Gene Expression Data," *Information Processing in Cells and Tissues*, Paton et al. (eds.), Plenum Publishing, pp. 203-212, 1998.

DeRisi et al., "Use of a cDNA Microarray to Analyse Gene Expression Patterns in Human Cancer," *Nature Genetics* vol. 14, pp. 457-460, Dec. 1996.

Schena et al., "Parallel Human Genome Analysis: Microarray-Based Expression Monitoring of 1000 Genes," *Proc. Natl. Acad. Sci., USA* vol. 93, pp. 10614-10619, Oct. 1996.

Dougherty et al., "Digital Measurement of Gene Expression in a cDNA Micro-Array," *SPIE* vol. 3034, pp. 68-72, Feb. 1997.

Zhou et al., *Microarray Biochip Technology*, BioTechniques Books, Schena (ed.), pp. 167-200, May 2000.

Baldi et al., *Bioinformatics: The Machine Learning Approach*, MIT Press, pp. 91-104, 1999.

Baldi et al., *Bioinformatics: The Machine Learning Approach*, MIT Press, pp. 105-141, 1999.

Devroye et al., *A Probabilistic Theory of Pattern Recognition*, pp. 507-547, 1999.

Jordan, *The Computer Science Engineering Handbook*, Tucker (ed.), CRC Press, pp. 536-556, 1997.

sci.nonlinear FAQ, *About Sci.nonlinear FAQ and Basic Theory* available at http://www.enm.bris.ac.uk/research/nonlinear/faq.html, May 1999.

Schena et al., "Quantitative Monitoring of Gene Expression Patterns with a Complementary DNA Microarray," *Science* vol. 270, pp. 467-470, Oct. 20, 1995.

D'Haeseleer et al., "Linear Modeling of mRNA Expression Levels During DNA Development and Injury," *Pac. Symp. Biocomput.*, pp. 41-52, 1999.

Eisen et al., "Cluster Analysis and Display of Genome-Wide Expression Patterns," *Proc. Natl. Acad. Sci. USA* vol. 95, pp. 14863-14868, Dec. 1998.

Eissa et al., "Multivariate Analysis of DNA Ploidy, p53, c-erbB-2 Proteins, EGFR, and Steroid Hormone Receptors for Prediction of Poor Short Term Prognosis in Breast Cancer," *Anticancer Res.* vol. 17, pp. 1417-1424, 1997.

Marchevsky et al., "Reasoning with Uncertainty in Pathology: Artificial Neural Networks and Logistic Regression as Tools for Prediction of Lymph Node Status in Breast Cancer Patients," *Mod. Pathol.* vol. 12, No. 5, pp. 505-513, 1999.

Shimizu et al., "Bioprocess Fault Detection by Nonlinear Multivariate Analysis: Application of an Artificial Autoassociative Neural Network and Wavelet Filter Bank," *Biotechnol. Prog.* vol. 14, pp. 79-87, 1998.

Spellman et al., "Comprehensive Identification of Cell-Cycle-Regulated Genes of the Yeast *Saccharomyces cerevisiae* by Microarray Hybridization," *Mol. Biol. Cell* vol. 9, pp. 2373-3297, Dec. 1998.

Spyratos et al., "Multiparametric Prognostic Evaluation of Biological Factors in Primary Breast Cancer," *J. Natl. Cancer Inst.* vol. 84, pp. 1266-1272, 1992.

Tavozic et al., "Systematic Determination of Genetic Network Architecture," *Nature Genetics* vol. 22, pp. 281-285, Jul. 1999.

Kingsbury, "Computational Biology," *The Computer Science and Engineering Handbook,* Tucker (ed.), CRC Press, pp. 959-975, 1997.

* cited by examiner

EXPERIMENT: SUBJECT CELLS TO CONDITION C AND OBSERVE CHANGE IN GENE EXPRESSION

FIG. 2

| EXPERIMENT | CELL LINE | CONDITION | G$_1$ | G$_2$ | G$_3$ | G$_4$ | ... | G$_N$ |
|---|---|---|---|---|---|---|---|---|
| 1 | A | C$_1$ | UP | DN | DN | UP | ... | UP |
| 2 | A | C$_2$ | UP | UN | UN | UN | ... | UN |
| 3 | A | C$_3$ | DN | UN | UN | UN | ... | UN |
| 4 | B | C$_1$ | UP | UN | UN | DN | ... | UN |
| 5 | B | C$_2$ | UP | UN | UN | UN | ... | UN |
| 6 | C | C$_1$ | DN | UN | DN | UN | ... | UN |
| ... | ... | ... | ... | ... | ... | ... | ... | ... |
| K | X | C$_H$ | UP | DN | UN | UN | ... | UN |

| | $G_1$ | $G_2$ | $C_1$ | $G_3$ (PREDICTED) | $G_3$ (OBSERVED) |
|---|---|---|---|---|---|
| $E_1$ | UP | UN | YES | UP | UP |
| $E_2$ | UP | UP | YES | UP | UP |
| $E_3$ | UN | DN | YES | UP | UP |
| $E_4$ | UN | UN | NO | DN | DN |
| $E_5$ | UP | DN | NO | DN | UP |
| $E_K$ | UP | UP | YES | UP | DN |

EFFECTIVENESS = 0.74

FIG. 21
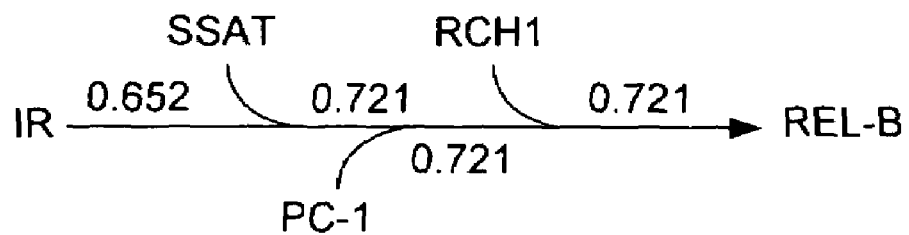
(A)
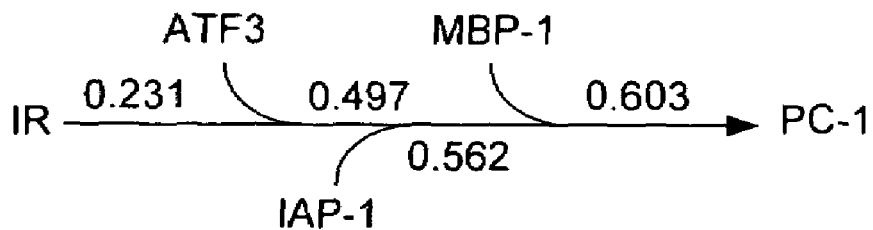
(B)
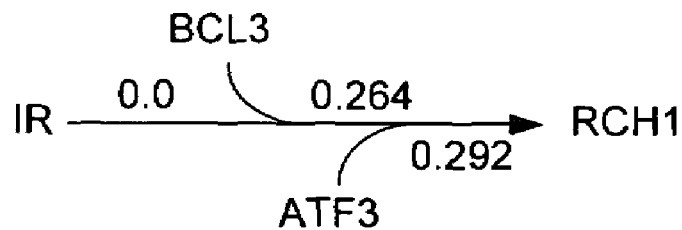
(C)
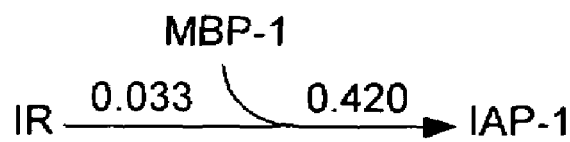
(D)

FIG. 19
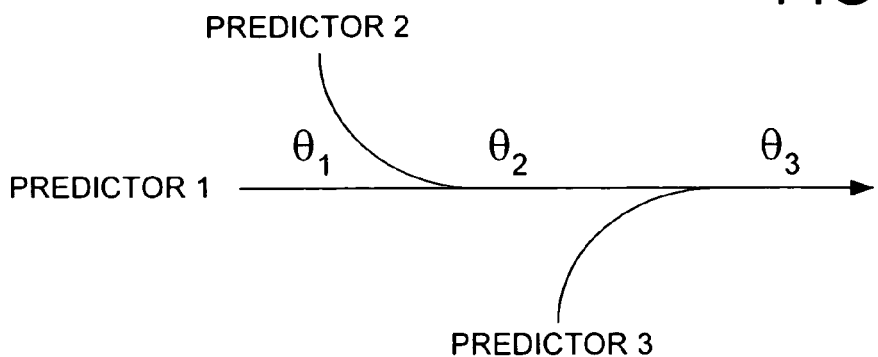
FIG. 20
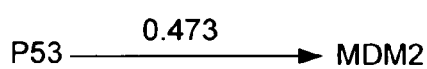
(A)
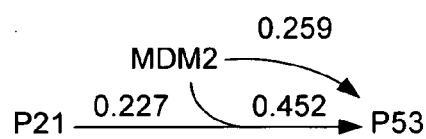
(B)
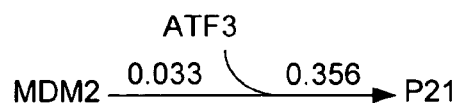
(C)

FIG. 22
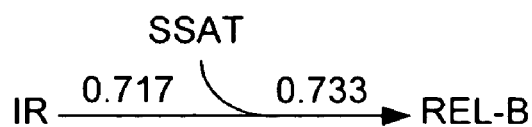
(A)
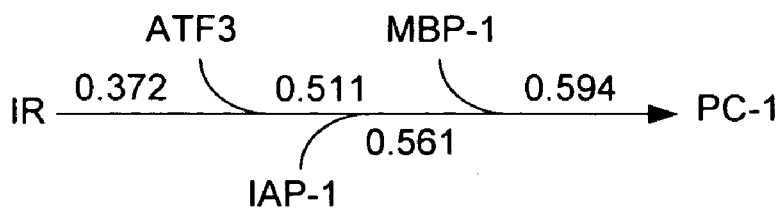
(B)
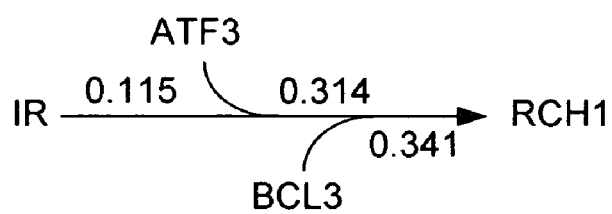
(C)
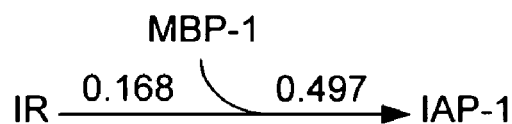
(D)

FIG. 23
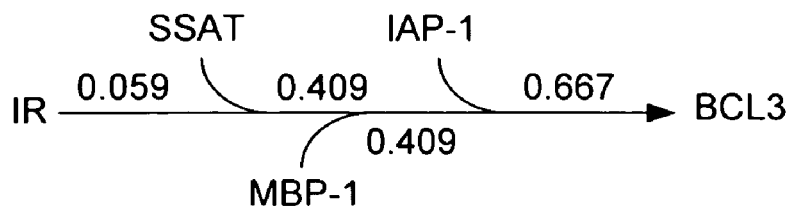
(A)
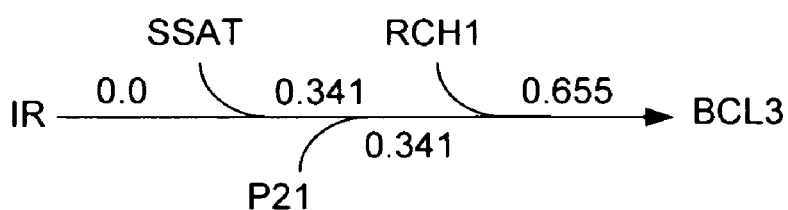
(B)
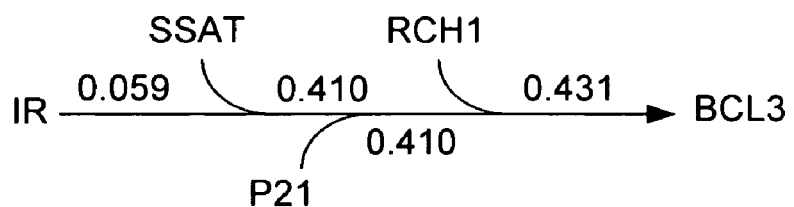
(C)
(D)

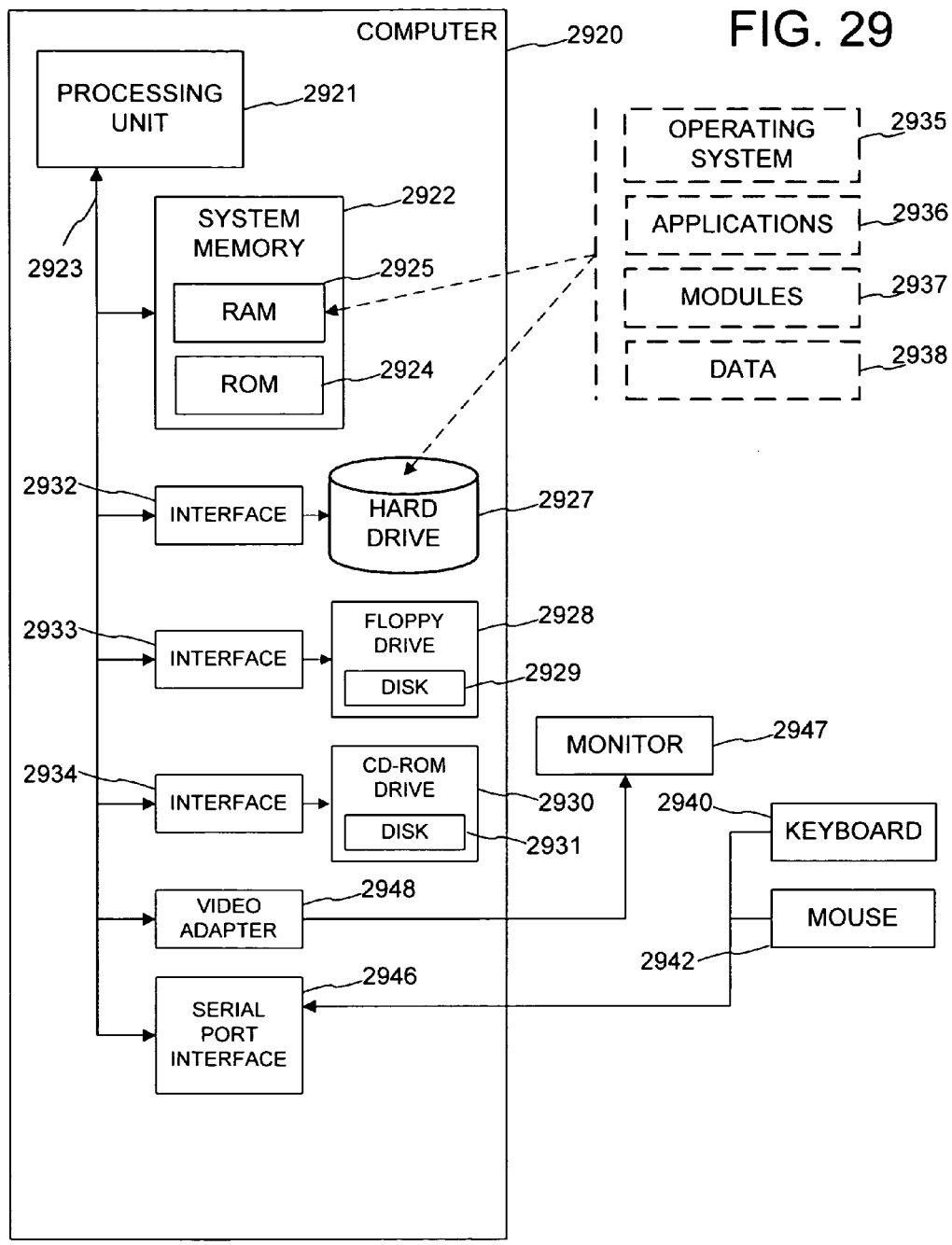

QUANTIFYING GENE RELATEDNESS VIA NONLINEAR PREDICTION OF GENE

FIELD

The invention relates to computer analysis of gene relationships.

BACKGROUND

The development of complementary DNA ("cDNA") microarray technology has provided scientists with a powerful analytical tool for genetic research (M. Schena, D. Shalon, R. W. Davis, and P. O. Brown, "Quantitative monitoring of gene expression patterns with a complementary DNA microarray," Science, 270[5235], 467–70, 1995). For example, a researcher can compare expression levels in two samples of biological material for thousands of genes simultaneously via a single microarray experiment. Application of automation to the microarray experiment processes further enhances researchers' ability to perform numerous experiments in less time. Consequently, an emerging challenge in the field of genetics is finding new and useful ways to analyze the large body of data produced by such microarray experiments.

Overview of Gene Biology

An organism's genome is present in each of its cells. The genome includes genes that hold the information necessary to produce various proteins needed for the cell's functions. For example, energy production, biosynthesis of component macromolecules, maintenance of cellular architecture, and the ability to act upon intra- and extracellular stimuli all depend on proteins.

Although the number of human genes is estimated to be 30,000 to 100,000, and each gene relates to a different protein, only a portion of the possible proteins are present ("expressed") in any individual cell. Certain proteins called "housekeeping" proteins are likely to be present in all cells. Other proteins that serve specialized functions are only present in particular cell types. For example, muscle cells contain specialized proteins that form the dense contractile fibers of a muscle. Although the exact combination of factors which specify the transcription rate of each particular protein at any given moment are often unknown, researchers have a general understanding of the mechanics and steps related to protein expression.

The expression of genetic information has been summarized in the "central dogma," which postulates that the flow of genetic information in a cell proceeds from DNA to RNA to protein. An initial step in the process of converting the genetic information stored in an organism's genome into a protein is called "transcription." Transcription essentially involves production of a corresponding mRNA molecule from a particular gene. The mRNA is later translated into an appropriate protein. One way to observe activity within the complex control network that is responsible for the generation of proteins within a cell is to observe transcript level (i.e., measuring the amount of mRNA) for a particular gene. The presence of a transcript from a gene indicates the biological system is taking the first steps to express a protein associated with the gene. This phenomenon is sometimes called "gene expression." Although complete operation of the mechanisms that control gene expression is not fully understood, users can gain insight into how the mechanisms operate by measuring expression levels for various genes.

A cDNA microarray experiment can produce data measuring gene expression levels for a large number of genes in biological material. One way to analyze these expression levels is to identify a pair of genes having a linear expression pattern under a variety of conditions.

For example, if the expression levels (e.g., "x" and "y") of two genes over a variety of observed conditions are plotted on a two-dimensional graph, it may be the case that a linear mathematical relationship ($y=mx+b$) is evident. To measure the linearity of the relationship between two genes, a researcher can calculate the Pearson correlation coefficient for points representing expression levels of the genes. A correlation coefficient with a high absolute value indicates a high degree of linear relationship between the two genes (i.e., if plotted in two-dimensional space, points representing the expression levels tend to fall in a line). Such genes are said to be "coexpressed." Coexpression does not necessarily indicate a cause-effect relationship. Still, given the immense volume of data collected for various sets of genes, discovering genes with linearly-related expression levels serves a useful purpose by identifying genes for further experimentation and study.

While identifying linearly-related gene pairs has led to various useful discoveries, there remains a need for other tools to analyze the wealth of data related to observation of gene expression levels.

SUMMARY

The invention provides methods and systems for analyzing data related to observation of gene expression levels. A nonlinear model can be constructed based on data comprising expression level observations for a set of genes. The nonlinear model predicts gene expression among the set of genes. The effectiveness of the nonlinear model in predicting gene expression can then be measured to quantify relatedness for genes in the set.

One implementation uses a full-logic multivariate nonlinear model. The effectiveness of the model can be tested for a set of predictive elements. The predictive elements are inputs that can include gene expression levels and an indication of the condition to which observed biological material was subjected (e.g., ionizing radiation).

Another implementation uses a neural network-based multivariate nonlinear model. For example, a ternary perceptron can be constructed with predictive elements as inputs and a predicted expression level for a predicted gene as an output. Effectiveness of the perceptron indicates relatedness among the predicted gene and genes related to the predictive elements.

Various techniques can be used to construct and measure the effectiveness of nonlinear models. For example, the same data can be used to both train and test a perceptron. Alternatively, the data can be divided into a training set and a test set. Further, the same data can be reused to train by randomly reordering the data. To avoid unnecessary computation, data for genes having expression levels not changing more than a minimum number of times can be ignored under certain circumstances.

Effectiveness of the nonlinear model can be measured by estimating a coefficient of determination. For example, a mean square error between a predicted value and a thresholded mean of observed values in a test data set can be calculated for the model.

Various user interface features allow users to interact with data in a variety of ways helpful for finding related genes. For example, a graph of a set of predictive elements and a predicted gene can show each predictive element's contribution to the effectiveness of predicting expression of the predicted gene via the size of a bar. The gene represented by a display element can be denoted by color. Further, redundant predictive element sets (e.g., a gene set in which one of the genes does not contribute to the effectiveness of the model) can be removed from a presentation of the analysis.

If the technique indicates a group of genes are related, researchers can then further investigate the group if appropriate.

Additional features and advantages of the invention will be made apparent from the following detailed description of illustrated embodiments, which proceeds with reference to the accompanying drawings.

BRIEF DESCRIPTION OF THE DRAWINGS

FIG. 2 is a table containing gene expression level data, such as that collected via a number of cDNA microarray experiments.

FIG. 19 is an exemplary arrow plot of a prediction tree showing coefficient of determination calculations.

FIGS. 20A–20C are arrow plots of prediction trees showing coefficient of determination calculations.

FIGS. 21A–D are arrow plots of prediction trees for full-logic predictors.

FIGS. 22A–D are arrow plots of prediction trees for perceptron predictors.

FIGS. 23A–D are arrow plots of prediction trees comparing full-logic and perceptron predictors.

FIG. 29 is a block diagram illustrating a computer system suitable as an operating environment for an implementation of the invention.

DETAILED DESCRIPTION

Definitions

Figure 1:
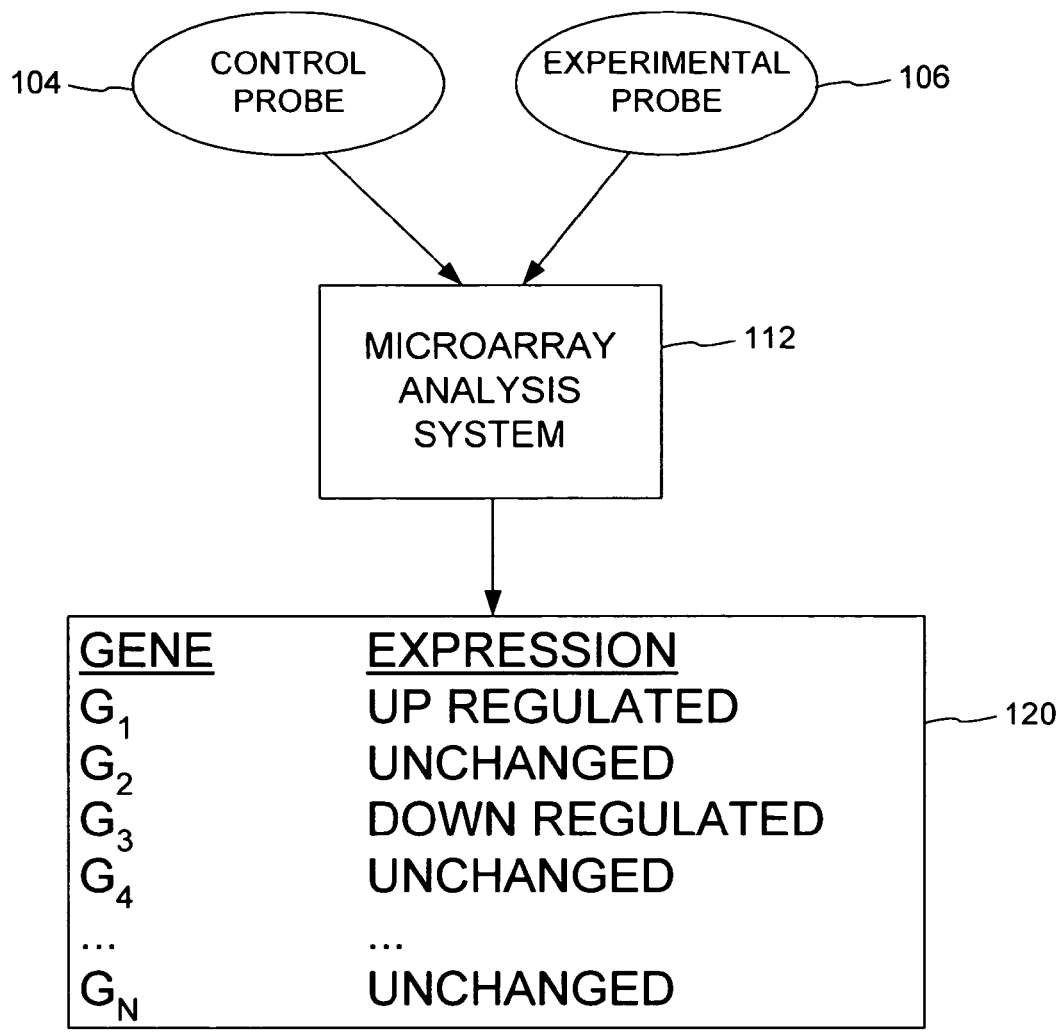
FIG. 1 is a diagram illustrating gene expression level data collection via a cDNA microarray experiment.

Additional definitions of terms commonly used in molecular genetics can be found in Benjamin Lewin, *Genes V* published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Gene relatedness includes genes having any of a variety of relationships, including coexpressed genes, coregulated genes, and codetermined genes. The mechanism of the relationship need not be a factor in determining relatedness. In the network that controls gene expression, a gene may be upstream or downstream from others; some may be upstream while others are downstream; or they may be distributed about the network in such a way that their relationship is based on chains of interaction among various intermediate genes or other mechanisms.

A probe comprises an isolated nucleic acid which, for example, may be attached to a detectable label or reporter molecule, or which may hybridize with a labeled molecule. For purposes of the present disclosure, the term "probe" includes labeled RNA from a tissue sample, which specifically hybridizes with DNA molecules on a cDNA microarray. However, some of the literature describes microarrays in a different way, instead calling the DNA molecules on the array "probes." Typical labels include radioactive isotopes, ligands, chemiluminescent agents, and enzymes. Methods for labeling and guidance in the choice of labels appropriate for various purposes are discussed, e.g., in Sambrook et al., in *Molecular Cloning: A Laboratory Manual*, Cold Spring (1989) and Ausubel et al., in *Current Protocols in Molecular Biology*, Greene Publishing Associates and Wiley-Intersciences (1987).

Hybridization: Oligonucleotides hybridize by hydrogen bonding, which includes Watson-Crick, Hoogsteen or reversed Hoogsteen hydrogen bonding between complementary nucleotide units. For example, adenine and thymine are complementary nucleobases which pair through formation of hydrogen bonds. "Complementary" refers to sequence complementarity between two nucleotide units. For example, if a nucleotide unit at a certain position of an oligonucleotide is capable of hydrogen bonding with a nucleotide unit at the same position of a DNA or RNA molecule, then the oligonucleotides are complementary to each other at that position. The oligonucleotide and the DNA or RNA are complementary to each other when a sufficient number of corresponding positions in each molecule are occupied by nucleotide units which can hydrogen bond with each other.

Specifically hybridizable and complementary are terms which indicate a sufficient degree of complementarity such that stable and specific binding occurs between the oligonucleotide and the DNA or RNA target. An oligonucleotide need not be 100% complementary to its target DNA sequence to be specifically hybridizable. An oligonucleotide is specifically hybridizable when there is a sufficient degree of complementarity to avoid non-specific binding of the oligonucleotide to non-target sequences under conditions in which specific binding is desired.

An experimental condition includes any number of conditions to which biological material can be subjected, including stimulating a cell line with ionizing radiation, ultraviolet radiation, or a chemical mutagen (e.g., methyl methane sulfonate, MMS). Experimental conditions can also include, for example, a time element.

Gene expression is conversion of genetic information encoded in a gene into RNA and protein, by transcription of a gene into RNA and (in the case of protein-encoding genes) the subsequent translation of mRNA to produce a protein. Hence, expression involves one or both of transcription or translation. Gene expression is often measured by quantitating the presence of mRNA.

Gene expression level is any indication of gene expression, such as the level of mRNA transcript observed in biological material. A gene expression level can be indicated comparatively (e.g., up by an amount or down by an amount) and, further, may be indicated by a set of discrete values (e.g., up-regulated, unchanged, or down-regulated).

A predictive element includes any quantifiable external influence on a system or a description of the system's state. In the context of gene expression, a predictive element includes observed gene expression levels, applied stimuli, and the status of biological material. In addition to those described below, possible external influences include use of pharmaceutical agents, peptide and protein biologicals, lectins, and the like. In addition to mutated or inactivated genes, possible cell states include transgenes, epigenetic elements, pathological states (e.g., cancer A or cancer B), developmental state, cell type (e.g., cardiomyocyte or hepatocyte), and the like. In some cases, combinations of predictive elements can be represented as a single logical predictive element.

Multivariate describes a function (e.g., a prediction function) accepting more than one input to produce a result.

Overview of Gene Expression Data

Although gene expression data has been collected in a variety of ways, advances in cDNA microarray technology have enabled researchers to increase the volume and accuracy of data collection. (Worley et al., "A Systems Approach to Fabricating and Analyzing DNA Microarrays," *Microarray Biochip Technology*, pp. 65–85, Schena, ed., Eaton Publishing, 2000). An overview of a cDNA microarray experiment is shown in FIG. 1. A cDNA microarray typically contains many separate target sites to which cDNA associated with respective genes has been applied. A single microarray may contain cDNA associated with thousands of genes.

During a process called hybridization, a sample with unknown levels of mRNA is applied to the microarray. After hybridization, visual inspection of the target site indicates a gene expression level for the gene associated with the target site. Further details concerning cDNA microarray technology can be found in Chen et al., U.S. patent application Ser. No. 09/407,021, filed on Sep. 28, 1999, entitled "Ratio Based Decisions and the Quantitative Analysis of cDNA Micro-Array Images" and Lockhart et al., U.S. Pat. No. 6,040,138, filed Sep. 15, 1995, entitled "Expression Monitoring by Hybridization to High Density Oligonucleotide Arrays," both of which are hereby incorporated herein by reference.

In a specific example of the cDNA microarray technique shown in FIG. 1, samples of mRNA from two different sources of biological material are labeled with different fluorescent dyes (e.g., Cy3 and Cy5). One of the samples (called a "control probe") 104 serves as a control and could be, for example, mRNA for a cell or cells of a particular cell line. The other sample (called an "experimental probe") 106, could be, for example, mRNA from the same cell line as the control probe, but from a cell or cells subjected to an experimental condition (e.g., irradiated with ionizing radiation).

Different fluorescent dyes are used so the two samples can be distinguished visually (e.g., by a confocal microscope or digital microscanner). The samples are sometimes called "probes" because they probe the target sites. The samples are then co-hybridized onto the microarray; mRNA from the sample (and the associated dye) hybridizes (i.e., binds) to the target sites if there is a match between mRNA in a sample and the cDNA at a particular target site. A particular target site is associated with a particular gene. Thus, visual inspection of each target site indicates how much (if any) mRNA transcript for the gene was present in the sample. For example, if the control probe is labeled with red dye, and a particular target site is associated with gene "A," abundant presence of the color red during visual inspection of the target site indicates a high gene expression level for gene "A" in the control probe. The intensity of the red signal can be correlated with a level of hybridized mRNA, which is in turn one measure of gene expression. The process thus can quickly provide gene expression level measurements for many genes for each sample.

The system 112 is typically a complex combination of subsystems that process the two samples 104 and 106 to quantify the hybridization of the probes to the microarray (and, thus the amount of mRNA transcript related to the gene in the probe and, therefore, the expression level of a gene associated with a target site). For example, a system 112 could comparatively quantify hybridization to produce results such as those shown in expression data 120. As shown, expression data 120 can specify expression comparatively (e.g., expression of the experimental probe vis-à-vis the control probe). Ratios of gene-expression levels between the samples are used to detect meaningfully different expression levels between the samples for a given gene. The phenomenon of observing an increase in the amount of transcript is called "up-regulation." A decrease is called "down-regulation." Although many of the details of the system 112 are not necessary for an understanding of the invention, the system 112 typically employs a wide variety of techniques to avoid error and normalize observations.

For example, system 112 can include a procedure to calibrate the data internally to the microarray and statistically determine whether the raw data justify the conclusion that expression is up-regulated or down-regulated with 99% confidence. (Chen et al., U.S. patent application Ser. No. 09/407,021, filed on Sep. 28, 1999, entitled "Ratio Based Decisions and the Quantitative Analysis of cDNA Micro-Array Images"). The system 112 can thus avoid error due to experimental variability.

As microarray technology progresses, the number of genes reliably measurable in a single microarray experiment continues to grow, leading to numerous gene expression observations. Further, automation of microarray experiments has empowered researchers to perform a large number of microarray experiments seriatim. As a result, large blocks of data regarding gene expression levels can be collected.

FIG. 2 shows gene expression level observations for a set of k microarray experiments. For the experiments, a variety of cell lines have been subjected to a variety of conditions, and gene expression level observations for n genes have been collected.

Although much data relating to gene expression can be collected, a major challenge for researchers is analyzing the data to determine whether genes in the experiment are related. As a result of careful analysis of a biological system, it may be possible to understand a portion of the control network responsible for controlling gene expression. These relationships are sometimes called "expression pathways" in the genetic network.

Figure 3:
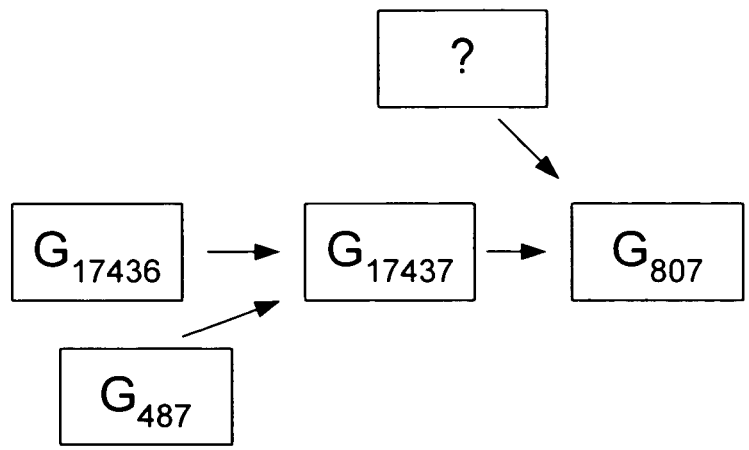
FIG. 3 is a diagram illustrating a simple representation of a gene expression pathway.

For example, a hypothetical expression pathway for a gene $G_{807}$ is shown in FIG. 3. In the example, expression of gene $G_{807}$ is the result of an as yet undiscovered mechanism in combination with expression of gene $G_{17437}$, which in turn is the result of expression of genes $G_{17436}$ and $G_{487}$. Discovery of an expression pathway represents a breakthrough in understanding of the system controlling gene expression and can facilitate a wide variety of advances in the field of genetics and the broader field of medicine. For example, if expression of $G_{807}$ causes a disease, blocking the pathway (e.g., with a drug) may avoid the disease.

Overview of Multivariate Nonlinear Models for Predicting Gene Expression

Figure 4:
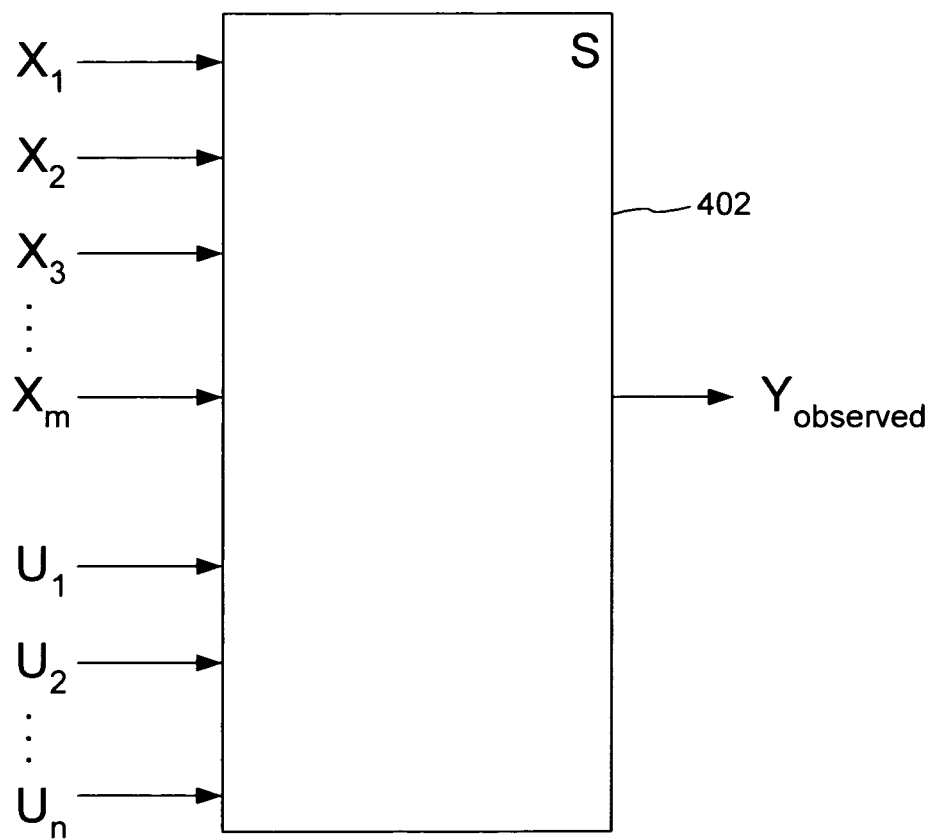
FIG. 4 is a block diagram representing a genetic system.

The system 402 responsible for expression of a particular gene can be represented as shown in FIG. 4. In the system 402, a set of observable inputs $X_1$-$X_m$ and a set of unknown inputs $U_1$-$U_n$ operate to produce an observed result, $Y_{observed}$ (or simply Y). Some of the observable inputs $X_1$-$X_m$ can correspond to gene expression levels. For the sake of example, it is assumed that the internal workings of the system 402 are beyond current understanding.

Figure 5:
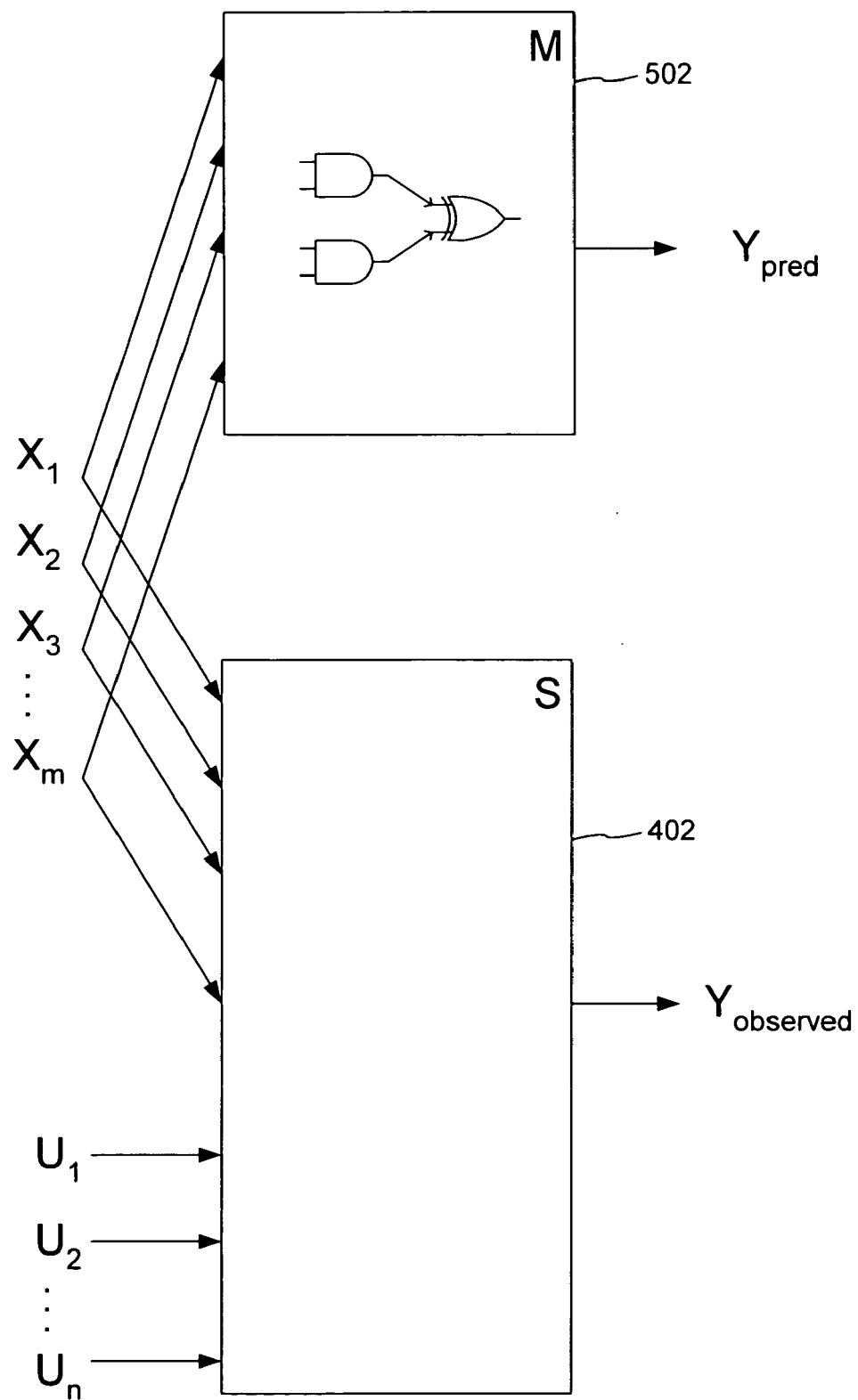
FIG. 5 is a block diagram representing a genetic system and an associated multivariate nonlinear model of the genetic system.

FIG. 5 shows a multivariate nonlinear model 502 for predicting the operation of the system 402. The model 502 is illustrated as comprising logic, but any multivariate nonlinear model can be used. The model 502 takes the observed inputs $X_1$-$X_m$ as inputs and provides a predicted output, $Y_{pred}$. In a model predicting gene expression, the inputs $X_1$-$X_m$ represent a set of predictive elements (e.g., gene expression levels, experimental conditions, or both), and Y represents the expression level of a predicted gene. The effectiveness of the multivariate nonlinear model 502 in predicting gene expression for the predicted gene can be measured to quantify the relatedness of the predicted gene and genes associated with the predictive elements. Measuring the effectiveness of the multivariate nonlinear model 502 can be accomplished by comparing $Y_{pred}$ and $Y_{observed}$ across a data set.

Figure 6:
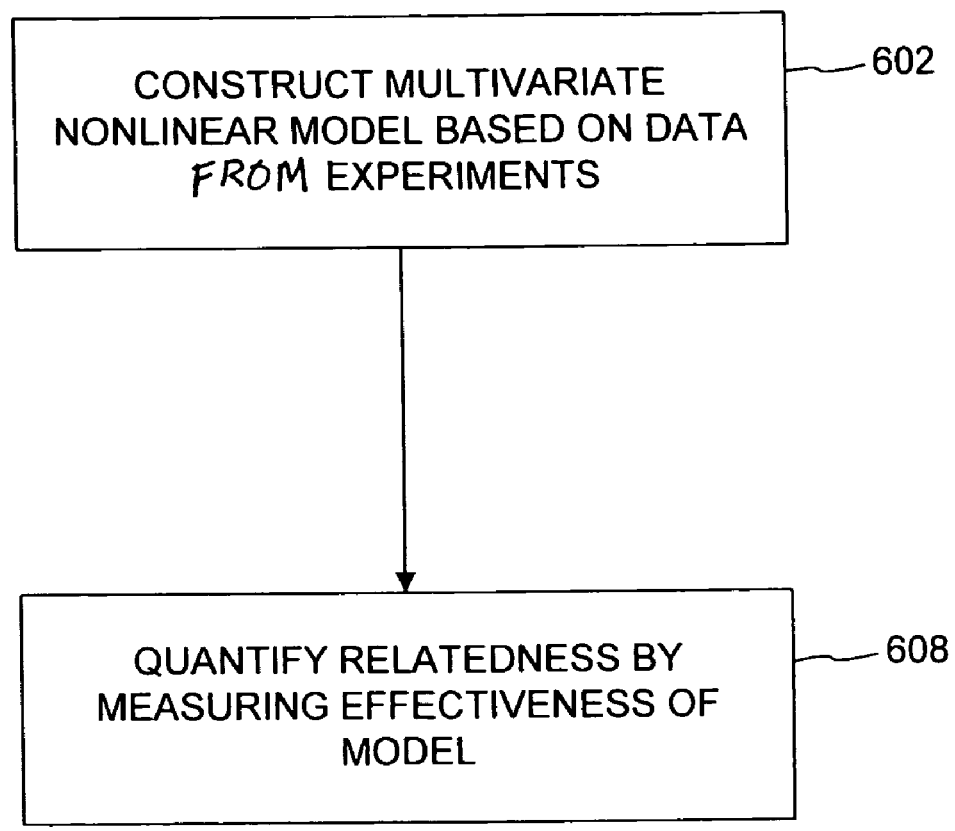
FIG. 6 is a flowchart showing a method for quantifying gene relatedness.

For example, a simple flowchart showing a method for quantifying gene relatedness is shown in FIG. 6. At 602, a multivariate nonlinear model is constructed based on data from gene expression level observation experiments. At 608, the effectiveness of the multivariate nonlinear model is measured to quantify gene relatedness. 608 can comprise predicting gene expression with the multivariate nonlinear model, then comparing predicted gene expression with observed gene expression.

Figures 7A, 7B:
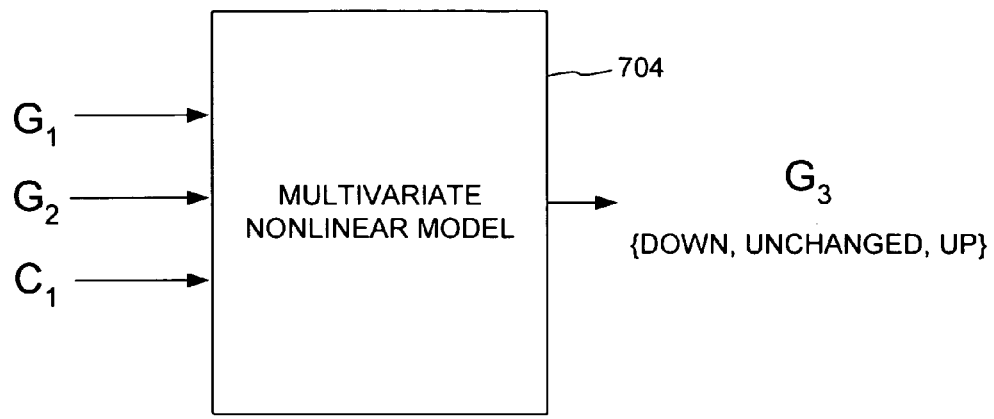
FIG. 7A is a block diagram showing a multivariate nonlinear predictor.
FIG. 7B is a table illustrating effectiveness measurement for the multivariate nonlinear predictor of FIG. 7A.

An exemplary multivariate nonlinear model 704, such as that constructed in 602 (FIG. 6), is shown at FIG. 7A. Construction of the model 704 is described in more detail below. The model 704 takes three inputs ($G_1$, $G_2$, and $C_1$) and produces a single output ($G_3$). In the example, the output is one of three discrete values chosen from the set {down, unchanged, and up}.

At FIG. 7B, a table 754 illustrates an exemplary measurement of the effectiveness of the model 704. Data collected during k microarray experiments is applied to the model 704, which produces a predicted value for $G_3$ for each experiment ($G_{3\ pred}$). In the example, effectiveness of the model 704 is calculated by comparing $G_{3\ pred}$ with $G_{3\ observed}$ across the data set comprising the experiments. Various methods can be used to measure effectiveness in such a technique. For example, the effectiveness of the model 704 can be compared with a proposed best alternative predictor (e.g., the thresholded mean of $G_{3\ observed}$). In the example, comparison with the thresholded mean of $G_{3\ observed}$ provides a value between 0 and 1 called the "coefficient of determination." The provided value can be said to estimate the coefficient of determination for an optimal predictor. For the model 704, a value of 0.74 is provided and quantifies the effectiveness of the model 704 and the relatedness of the genes $G_1$, $G_2$, and $G_3$ (and the condition $C_1$). In the example, a high value indicates more relatedness than a low value, and the value falls between 0 and 1. However, any number of other conventions can be used (e.g., a percentage or some other rating).

The above techniques can be expanded for application to a large set of observed genes (i.e., genes for which gene expression levels have been observed). For example, FIG. 8 shows a method for analyzing gene expression data to quantify relatedness among a large set of i genes.

At 802, one of the observed genes is designated as a predicted gene. Typically, for each of the predicted genes, 808–820 are repeatedly performed. At 808, a set of predictive elements (e.g., gene expression levels, experimental conditions, or both) are designated for the predicted gene. At 812, a multivariate nonlinear model based on data from the experiments is constructed having the predictive elements as inputs and the predicted gene as an output. At 816, the effectiveness of the model in predicting expression of the predicted gene is measured to quantify relatedness of the predictive elements and the predicted gene.

At 820, if there are more possible permutations of predictive elements for the predicted gene, the method proceeds to 808. Otherwise, at 832, if there are more possible genes to be predicted, the method proceeds to 802, and another predicted gene is chosen. Although the method is shown as a loop, it could be performed in some other way (e.g., in parallel).

Figure 8:
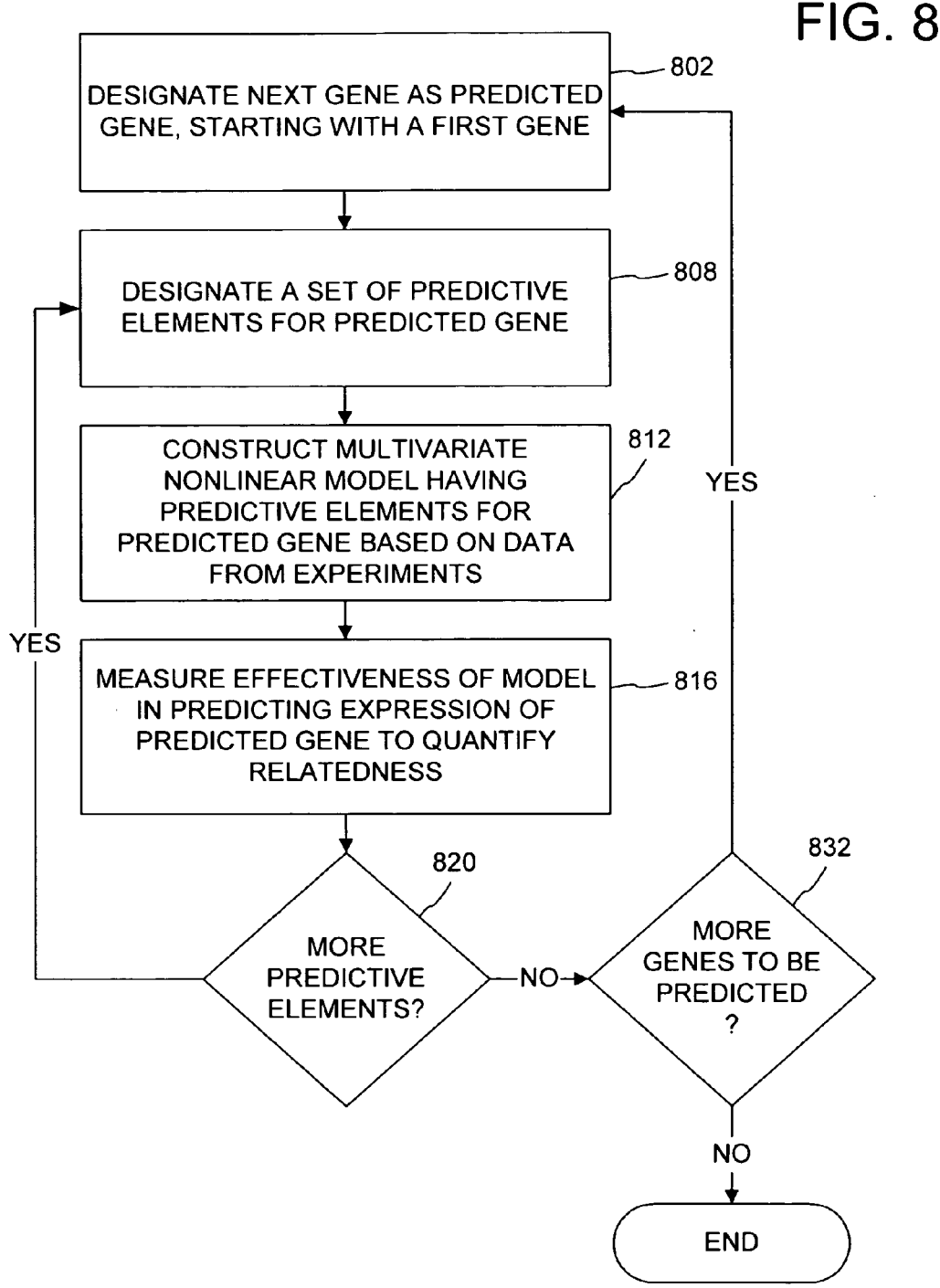
FIG. 8 is a flowchart showing a method for identifying related genes out of a set of observed genes.

Exemplary data for use with the method of FIG. 8 is shown in Table 1, where "+1," "0," and "−1" represent up-regulation, unchanged, and down-regulation, respectively. For the j conditions $C_1$–$C_j$, "y" means the experimental sample was subjected to the indicated condition, and "n" means the experimental sample was not.

TABLE 1

Gene Expression Data for i Genes over k Experiments

| Experiment | $G_1$ | $G_2$ | $G_3$ | ... | $G_i$ | $C_1$ | $C_2$ | ... | $C_j$ |
|---|---|---|---|---|---|---|---|---|---|
| $E_1$ | +1 | +1 | −1 | ... | 0 | y | n | ... | n |
| $E_2$ | 0 | +1 | −1 | ... | 0 | n | y | ... | n |
| $E_3$ | −1 | 0 | −1 | ... | 0 | n | n | ... | y |
| $E_4$ | −1 | 0 | 0 | ... | 0 | y | n | ... | n |
| $E_5$ | +1 | 0 | 0 | ... | 0 | n | y | ... | n |
| ... | ... | ... | ... | ... | ... | ... | ... | ... | ... |
| $E_k$ | −1 | −1 | 0 | ... | +1 | n | n | ... | y |

Exemplary results of the analysis of the data shown in Table 1 are shown in Table 2. In the example, results for groups of three predictive elements are shown. Typically, results for groups of other sizes (e.g., two) are also provided. As described in further detail below, it is also possible to omit results or skip genes under certain circumstances.

According to the results, relatedness of the genes $G_2$, $G_3$, $G_5$, and $G_1$ is 0.71 (based on a model with $G_1$ as the predicted gene), and relatedness of the genes $G_2$, $G_3$, $G_1$, and condition $C_1$ is 0.04 (based on another model).

TABLE 2

Results of Analysis of Gene Expression Data of Table 1

| Predictors | | | Predicted | |
|---|---|---|---|---|
| $X_1$ | $X_2$ | $X_3$ | gene | Relatedness |
| $G_2$ | $G_3$ | $G_4$ | $G_1$ | 0.21 |
| $G_2$ | $G_3$ | $G_5$ | $G_1$ | 0.71 |
| ... | ... | ... | ... | ... |
| $C_1$ | $G_2$ | $G_3$ | $G_1$ | 0.04 |
| $C_1$ | $G_2$ | $G_4$ | $G_1$ | 0.17 |
| $C_1$ | $G_2$ | $G_5$ | $G_1$ | 0.67 |
| ... | ... | ... | ... | ... |
| $G_1$ | $G_3$ | $G_4$ | $G_2$ | 0.26 |
| $G_1$ | $G_3$ | $G_5$ | $G_2$ | 0.73 |
| $G_1$ | $G_3$ | $G_6$ | $G_2$ | 0.09 |
| ... | ... | ... | ... | ... |

Exemplary Multivariate Nonlinear Models Predicting Gene Expression

A wide variety of multivariate nonlinear models for predicting gene expression are possible, and they may be implemented in software or hardware. For example, the form of a full-logic model having three ternary inputs $X_1$, $X_2$, and $X_3$ and one ternary output $Y_{pred}$ is shown in Table 3. The full-logic model shown takes the form of a ternary truth table. Constructing the illustrated full-logic model thus involves choosing values for at least some of $y_1$–$y_{27}$ from the set {−1, 0, +1} to represent gene expression. Although the term "full-logic" typically implies that a value will be chosen for each possible y, it is possible to delay or omit choosing a value for some y's and still arrive at useful results.

The number of inputs can vary and a convention other than ternary can be used. If there are m input variables, then the table has $3^m$ rows and m+1 columns, and there are $3^{3^m}$ possible models.

TABLE 3

Full-logic Multivariate Nonlinear Model

| $X_1$ | $X_2$ | $X_3$ | $Y_{pred}$ |
|---|---|---|---|
| −1 | −1 | −1 | $y_1$ |
| −1 | −1 | 0 | $y_2$ |
| −1 | −1 | 1 | $y_3$ |
| −1 | 0 | −1 | $y_4$ |
| −1 | 0 | 0 | $y_5$ |
| −1 | 0 | 1 | $y_6$ |
| −1 | 1 | −1 | $y_7$ |
| −1 | 1 | 0 | $y_8$ |
| −1 | 1 | 1 | $y_9$ |
| 0 | −1 | −1 | $y_{10}$ |
| 0 | −1 | 0 | $y_{11}$ |
| 0 | −1 | 1 | $y_{12}$ |
| ... | ... | ... | ... |
| 1 | 1 | 1 | $y_{27}$ |

Constrained and Unconstrained Models

The illustrated full-logic model is sometimes called an "unconstrained" model because its form can be used to represent any of the $3^{3^m}$ theoretically possible models. Under certain circumstances (e.g., when relatively few data points are available), it may be advantageous to choose the model from a constrained set of models.

Figure 9:
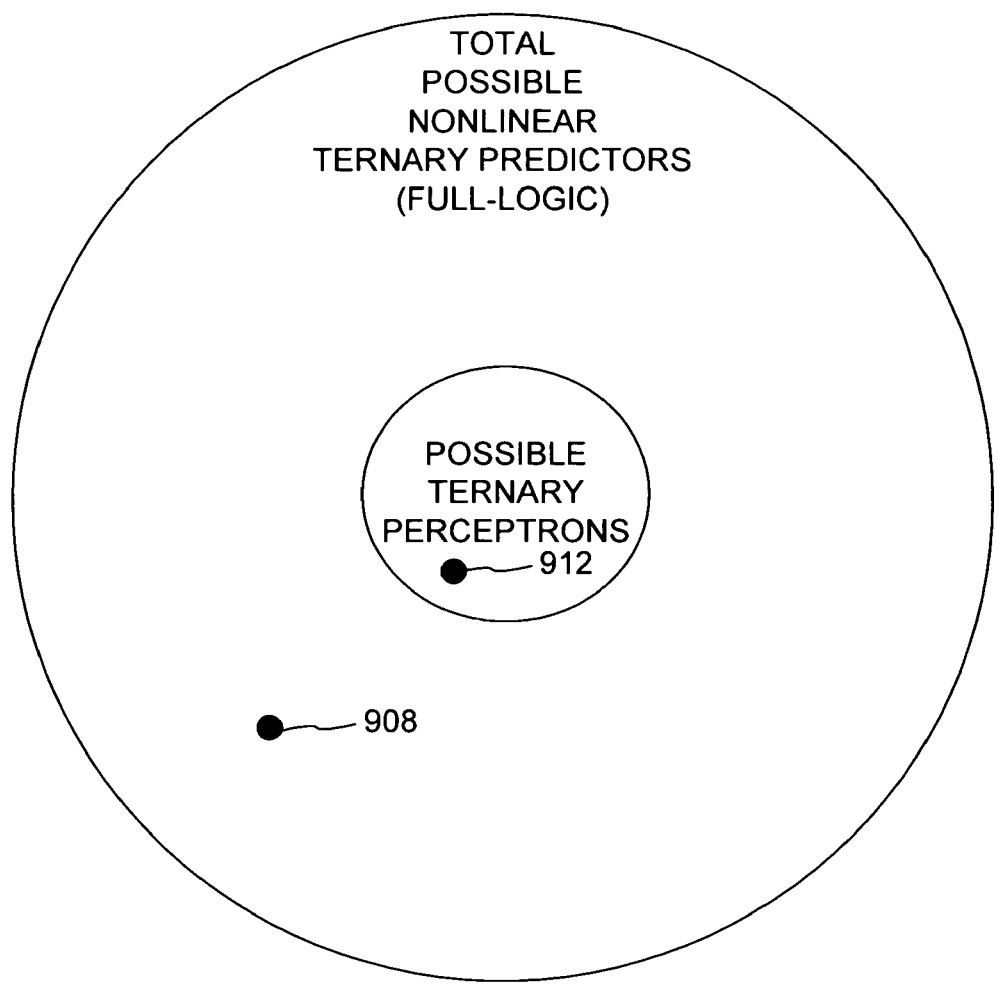
FIG. 9 is a Venn diagram showing a relationship between unconstrained and constrained predictors.

For example, another possible multivariate nonlinear model is a neural network. A ternary perceptron is a neural network with a single neuron. As shown in FIG. 9, there are fewer possible ternary perceptrons than full-logic models, so ternary perceptrons are sometimes called "constrained" models. Any number of other constraints can be imposed. For example, a truth table or decision tree may take a constrained form.

In some sense, it is desirable to choose the optimal (i.e., best) model; however, it is sometimes unknown whether the optimal model can be found within a constrained set of models. For example, it may be that the optimal model is model 908, which would not be found if the models are constrained to ternary perceptrons. On the other hand, the optimal model may be model 912, which can be represented by either a full-logic model or a ternary perceptron. Deciding whether to use constrained or unconstrained models typically depends on the sample size, as it can be shown that choosing from constrained models can sometimes reduce the error associated with estimating the coefficient of determination when the sample size is small. Further details concerning the phenomenon are provided in a later section.

Exemplary Perceptron

Figure 10:
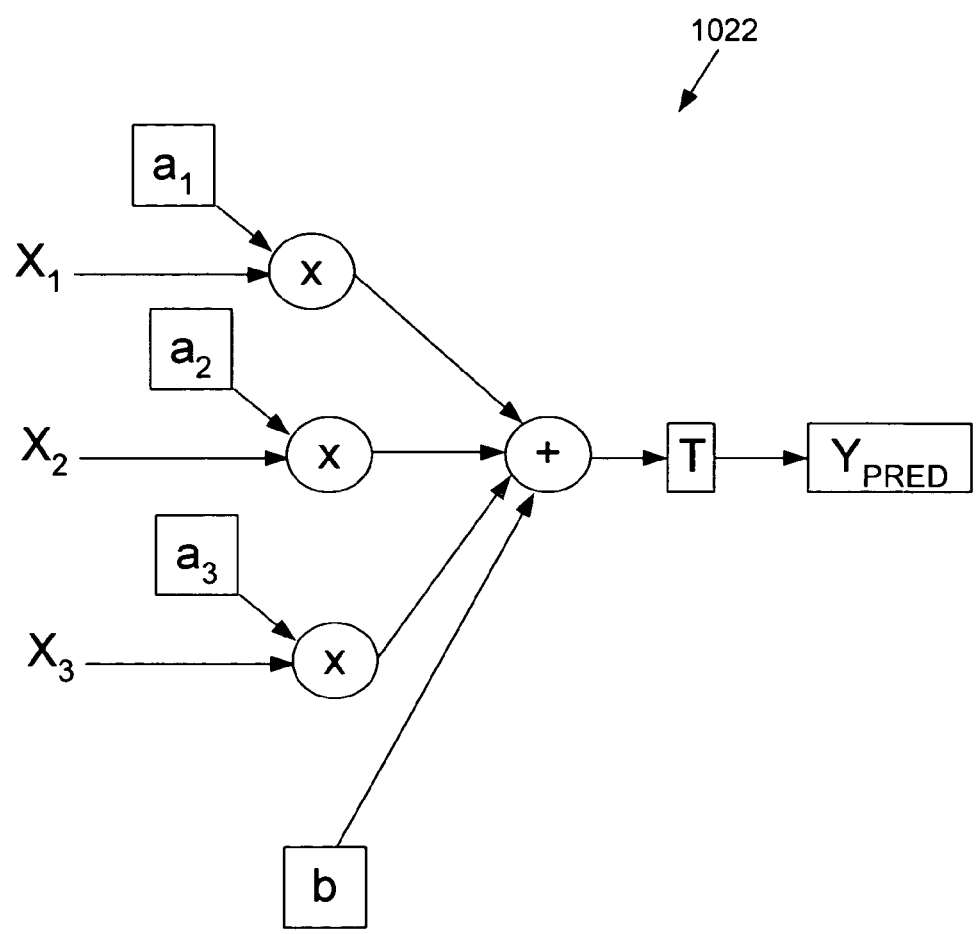
FIG. 10 is a diagram showing a graphical representation of a perceptron multivariate nonlinear model for predicting gene expression for a predicted gene.

A perceptron can be represented by the equation $$Y_{pred} = T(a_1 X_1 + a_2 X_2 + \ldots + a_m X_m + b) \quad (1)$$

where T is a thresholding function, $X_1, X_2 \ldots X_m$ are inputs, $Y_{pred}$ is an output, and $a_1, a_2 \ldots a_m$ and b are scalars defining a particular perceptron. For a binary perceptron, a binary threshold function is used: $T(z)=0$ if $z \leq 0$, and $T(z)=1$ if $z>0$. For a ternary perceptron, a ternary threshold function is used:

$T(z)=-1$ if $z<-0.5$, $T(z)=0$ if $-0.5 \leq z \leq 0.5$, and $T(z)=+1$ if $z>0.5$ FIG. 10 shows one possible graphical representation 1022 of the perceptron shown in Equation 1. Thus, to design the perceptron, $a_1$–$a_m$ and b are chosen based on observed gene expression levels. Typically, designing the perceptron involves a training method, explained in detail below.

Exemplary User Interface for Presenting Results

Figure 11:
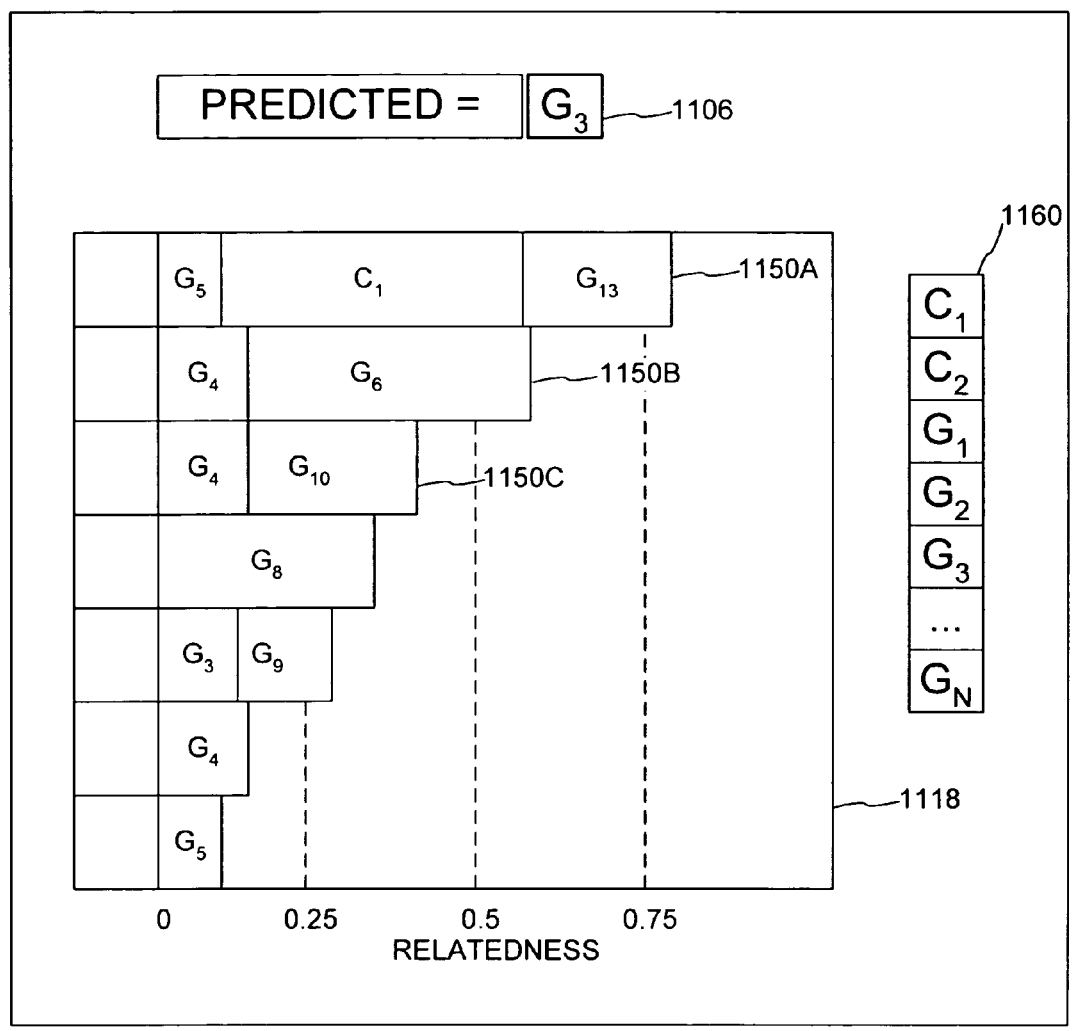
FIG. 11 is a screen capture showing an exemplary user interface for presenting effectiveness of predictors constructed to predict gene expression among a variety of gene groups.

An exemplary user interface for presenting data similar to that of Table 2 is shown in the display region 1102 of FIG. 11. Data can be limited to a particular predicted gene (sometimes called a "target gene") by specifying the gene in box 1106. Results pane 1118 displays a set of bars 1150a, 1150b, and 1150c. Each of the bars represents a set of predictive elements used in a particular multivariate nonlinear model to predict the predicted gene of box 1106. Effectiveness of the model is indicated by the size of the bar. Further, each predictive element's contribution to the effectiveness of the model is indicated by the size of the bar segment representing the predictive element.

There are various ways to assign a contribution for each element. For example, consider a set of three predictive elements having a combined measure of effectiveness. A first element with the highest effectiveness when used alone (e.g., in a univariate model) is assigned a contribution of the measured effectiveness when used alone (i.e., the effectiveness of the univariate model). Then, effectiveness of the most effective pair of predictive elements including the first element is measured, and the second element of the pair is assigned a contribution equal to the effectiveness of the pair minus the effectiveness of the first element. Finally, the third element of the pair is assigned a contribution to account for any remaining effectiveness of the three combined elements.

As shown, the bars are ordered (i.e., the more effective models are shown at the top). Additionally, the appearance of each predictive element within the bars can be ordered. By default, the predictive elements are ordered within the bars by contribution to effectiveness (e.g., genes with larger contribution are placed first). However, a user may choose to order them so that a particular predictive element appears in a consistent location. For example, the user may specify that a particular predictive element appear first (e.g., to the left) inside the bar.

To aid in visual interpretation of the data, a legend 1160 is presented Although the legend is shown in black and white in the drawing in an implementation, a legend is presented in which each predictive element is shown in a box of a particular color. In the implementation, the bars 1150a, 1150b, and 150c take advantage of the legend 1160 by representing each predictive element in the color as indicated in the legend 1160. As explained in greater detail below, a wide variety of alternative or additional user interface features can be incorporated into the user interface.

Details of Exemplary Implementations

Figure 12:
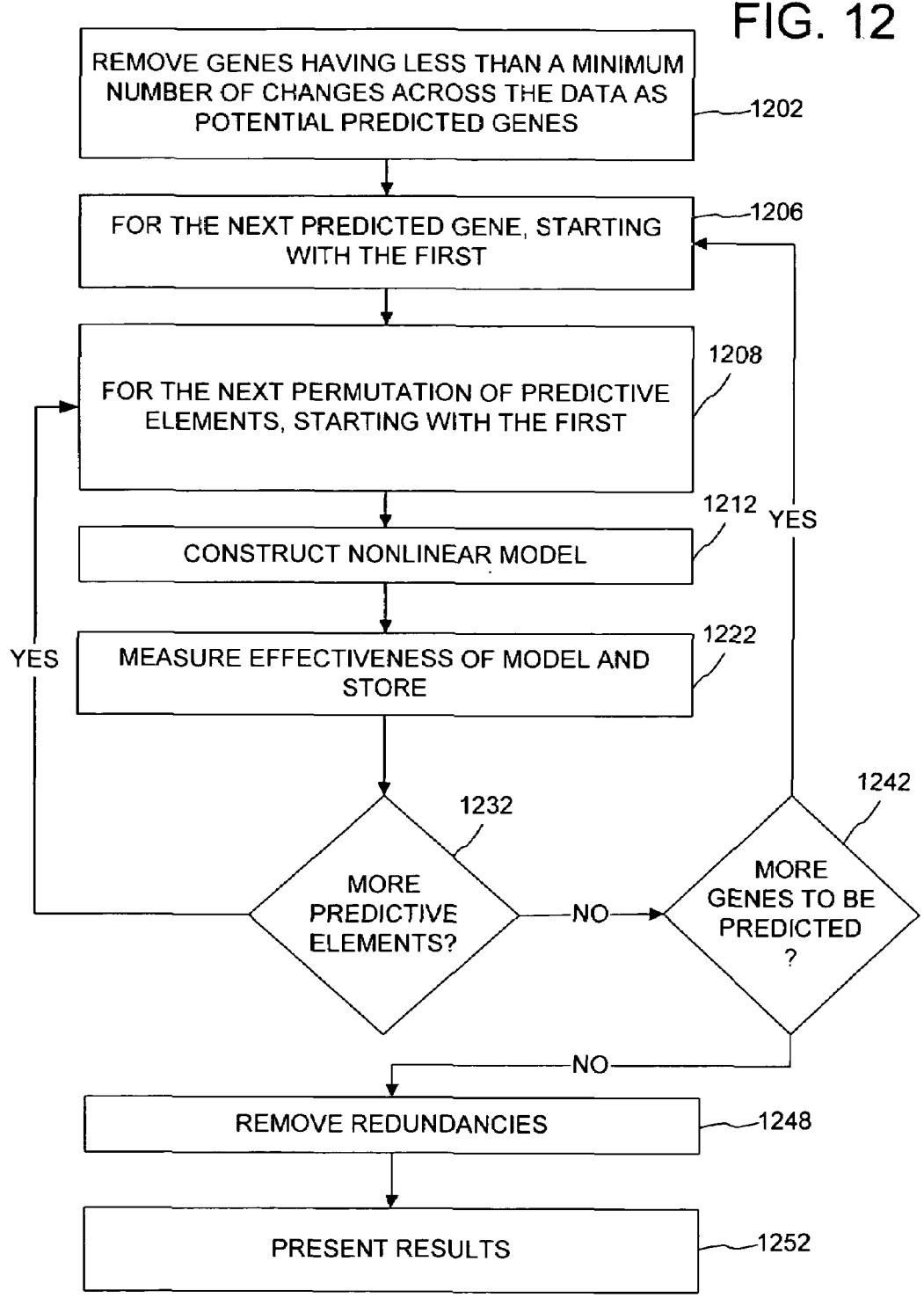
FIG. 12 is a flowchart showing a method for analyzing gene expression data to identify related genes.

A more detailed method for quantifying gene relatedness via multivariate nonlinear prediction of gene expression is shown in FIG. 12. The method can use data similar to that shown for Table 1 and quantifies gene relatedness by estimating a coefficient of determination. For example, an experiment involving a collection of microarrays might measure relatedness for 8,000 genes.

At 1202, genes having fewer than a minimum number of changes (e.g., 12%) are removed as potential predicted genes. In this way, unnecessary computation regarding genes providing very little information is avoided.

At 1206, one of the remaining genes is selected as the predicted (or "target") gene. For a given predicted gene, the method computes coefficients of determination for possible combinations of one, two, and three predictive elements. A restriction on the number of genes can assist in timely computation of greater numbers of predictive elements (e.g., four). Depending on the number of microarrays in the experiments, results yielded by excessive predictive elements may not be meaningful.

At 1208, a set of predictive elements is selected. Then, at 1212, a multivariate nonlinear model is constructed for the predictive elements and the predicted gene. The set of data used to construct the model is sometimes called the "training data set."

At 1222, the effectiveness of the multivariate nonlinear model is measured to quantify relatedness between the predicted gene and genes associated with the predictive elements. In the example, a coefficient of determination is calculated. The data used to measure the model's effectiveness is sometimes called the "test data set." The test data set may be separate from, overlap, or be the same as the training data set. A variety of techniques can be used to improve estimation of the coefficient of determination. For example, multiple attempts can be made using subsets of the data and an average taken. The coefficient of determination is stored in a list for later retrieval and presentation.

At 1232, it is determined whether there are more permutations of predictive elements for the predicted gene. If so, the method continues at 1208. Otherwise, at 1242 it is determined whether there are more genes to be designated as a predicted gene. If so, the method continues at 1206. Although the method is shown as a loop, it could be performed in some other way (e.g., in parallel).

Then, at 1248, redundancies are removed from the list of coefficients of determination. For a set of predictive elements, one or more of the predictive elements may not contribute to the coefficient of determination. Data relating to these predictive elements is removed. For example, if predictive elements "A" and "B" predict "Y" with a coefficient of determination of 0.77 and "A," "B," and "C" predict "Y" at 0.77, the data point for "A," "B," and "C" is redundant and is thus removed.

The results (i.e., the list of coefficients of determination) are then presented at 1252. A variety of user interface features can assist in analysis of the results as described in more detail below.

A variety of multivariate nonlinear models for predicting gene expression are possible. Full-logic and neural network implementations are described below.

Full-Logic Predictor

Figure 13:
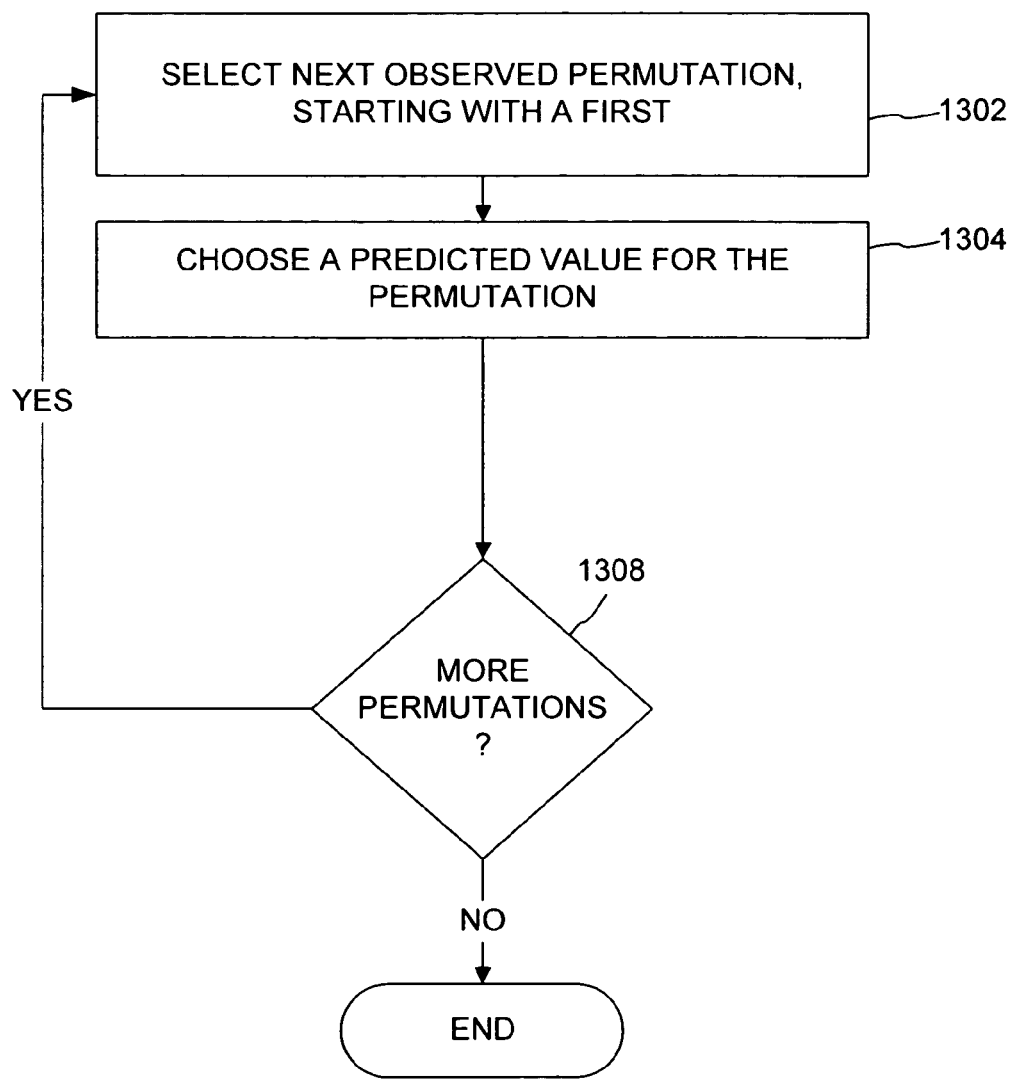
FIG. 13 is a flowchart showing a method for constructing a full-logic model to predict gene expression.

A method for constructing a full-logic multivariate nonlinear model to predict gene expression is illustrated in FIG. 13. The model can be built using data such as that shown in Table 1. Typically, the inputs and output of the model are chosen, then the model is built based on those inputs and outputs. For example, the inputs might be an expression level for gene "A," and expression level for gene "B," and an experimental condition "C." The output is a prediction of the expression level for gene "Y."

At 1302, a next observed permutation is selected, starting with the first. It may be that all possible permutations of the three inputs appear in the data (e.g., all possible arrangements of "−1," "0," and "+1" are present for inputs "A," "B," and "C"). However, some permutations may not appear.

At 1304, a predicted value is chosen for the permutation. In some cases, a single result (e.g., "−1") will be observed for all instances of a particular permutation. In such a case, the predicted value is the result (i.e., "−1"). In other cases, there may be two results observed. In such a case, the result with the most instances is chosen. In still other cases, there may be more than two results observed. In such a case, a thresholded weighted mean is chosen as the predicted value.

If there are more observed permutations, at 1308, the method proceeds to 1302. After completion, the full-logic model has been built. The full-logic value can then supply a predicted value given a particular permutation of predictive elements.

Figure 14:
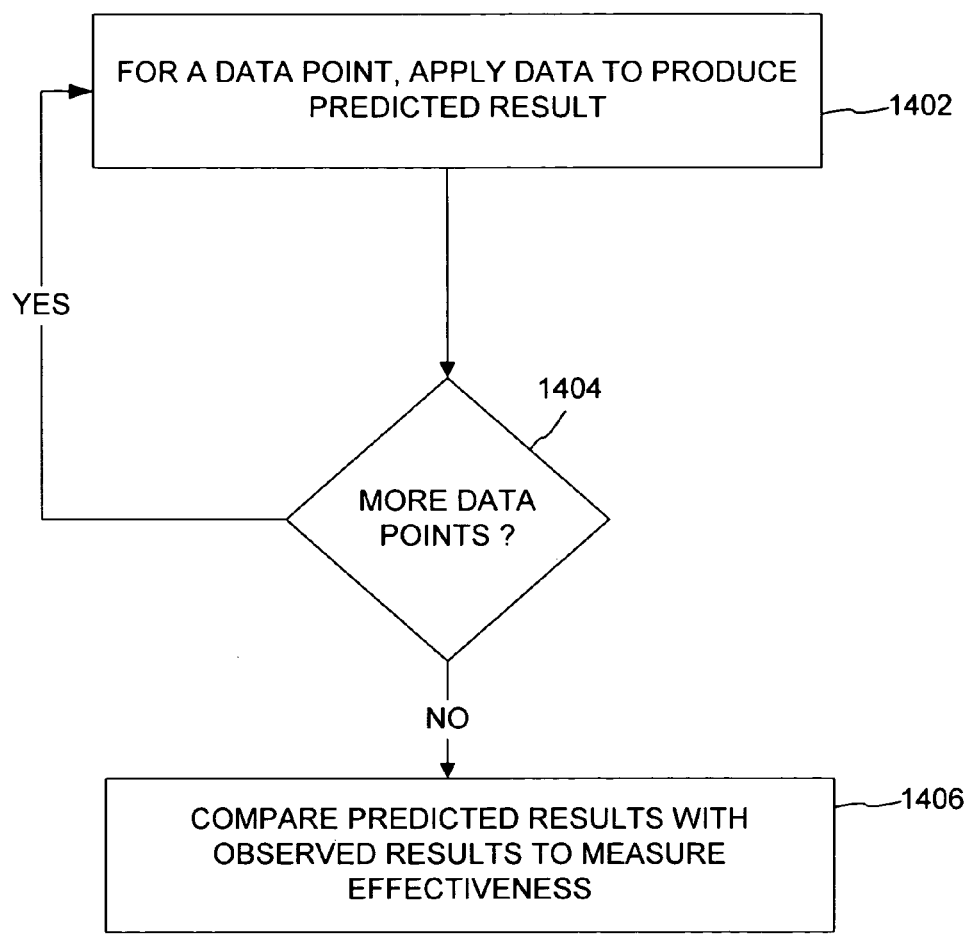
FIG. 14 is a flowchart showing a method for testing the effectiveness of a full-logic model in predicting gene expression.

A method for testing a full-logic model to measure the coefficient of determination is shown in FIG. 14. For each data point in the testing set (e.g., a row of data), the data point applied to the model (i.e., submitted as predictive elements) to produce a predicted result at 1402. If there are more data points, at 1404, the method proceeds to 1402.

Then, at 1406, the predicted results are compared with the observed results to measure effectiveness of the model. A coefficient of determination ($\theta$) is estimated using the following equation:

$$\theta = \frac{\sum_{i=1}^{n} \frac{(T(\mu Y) - Y_i)^2}{n} - \sum_{i=1}^{n} \frac{(Y_{pred_i} - Y_i)^2}{n}}{\sum_{i=1}^{n} \frac{(T(\mu Y) - Y_i)^2}{n}} \quad (2)$$

where n is the number of data points submitted as a test data set, T is a thresholding function, and $\mu_Y$ is the mean of observed values of Y. $Y_i$ is the observed Y at a particular data point in the test data, and $Y_{pred_i}$ is the corresponding value predicted for Y by the full-logic model at the same data point (via the predictive elements for the data point).

Note that the predicted results can be stored for comparison at the end of the method or compared as the method proceeds. Other approaches can be used to achieve similar results.

In some instances, it may be that the prediction for the full-logic model is undefined for a set of inputs (e.g., the permutation of input variables was not observed in the training data set). In such a case, a variety of approaches are possible, and various rules exist for defining output. For example, a technique called "nearest neighbor" can be employed to pick a value, the value may be defined as an average of neighbors, or the value may simply be defined as "0."

Neural Network Predictor

Figure 15:
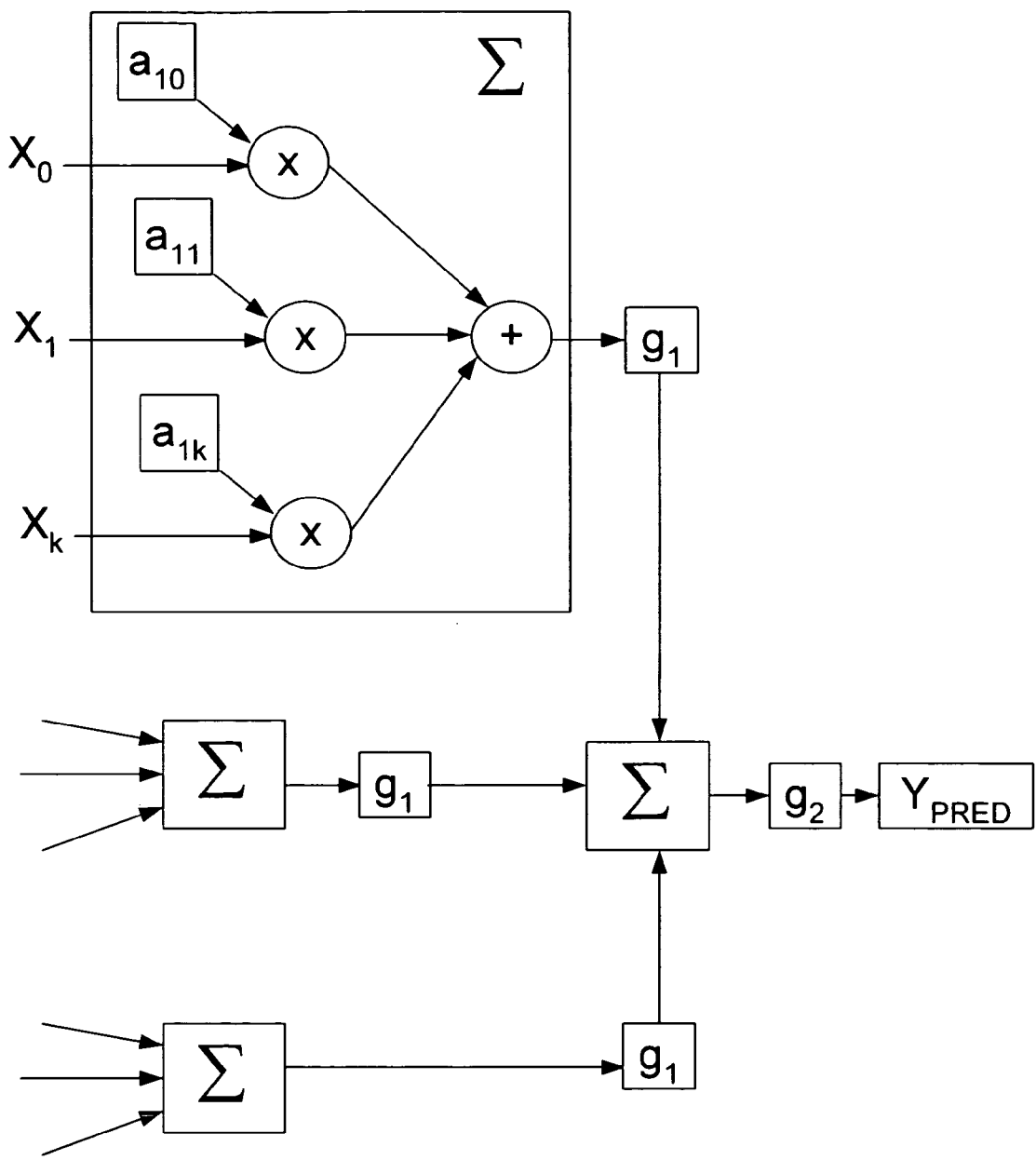
FIG. 15 is a flowchart showing a diagram of a two-layer neural network.

Neural networks offer a multivariate nonlinear model which can be trained in order to construct an artificial intelligence function. Constraint can be increased or decreased based on the form of the network. A wide variety of neural network forms are possible. A two-layer neural network is of the form $$Y_{pred} = g_2\left(\sum_{j=0}^{r} a_j g_1\left(\sum_{k=0}^{m} a_{jk} X_k\right)\right) \quad (3)$$

where $X_k$ are the input variables ($X_0 \equiv 1$), and $g_1$ and $g_2$ are the activation functions for the first and second layers, respectively. A diagram of a two-layer neural network is shown in FIG. 15. There are a number of training algorithms available for neural networks, one of which is explained below.

Training a Perceptron to Predict Gene Expression Levels

Figure 16:
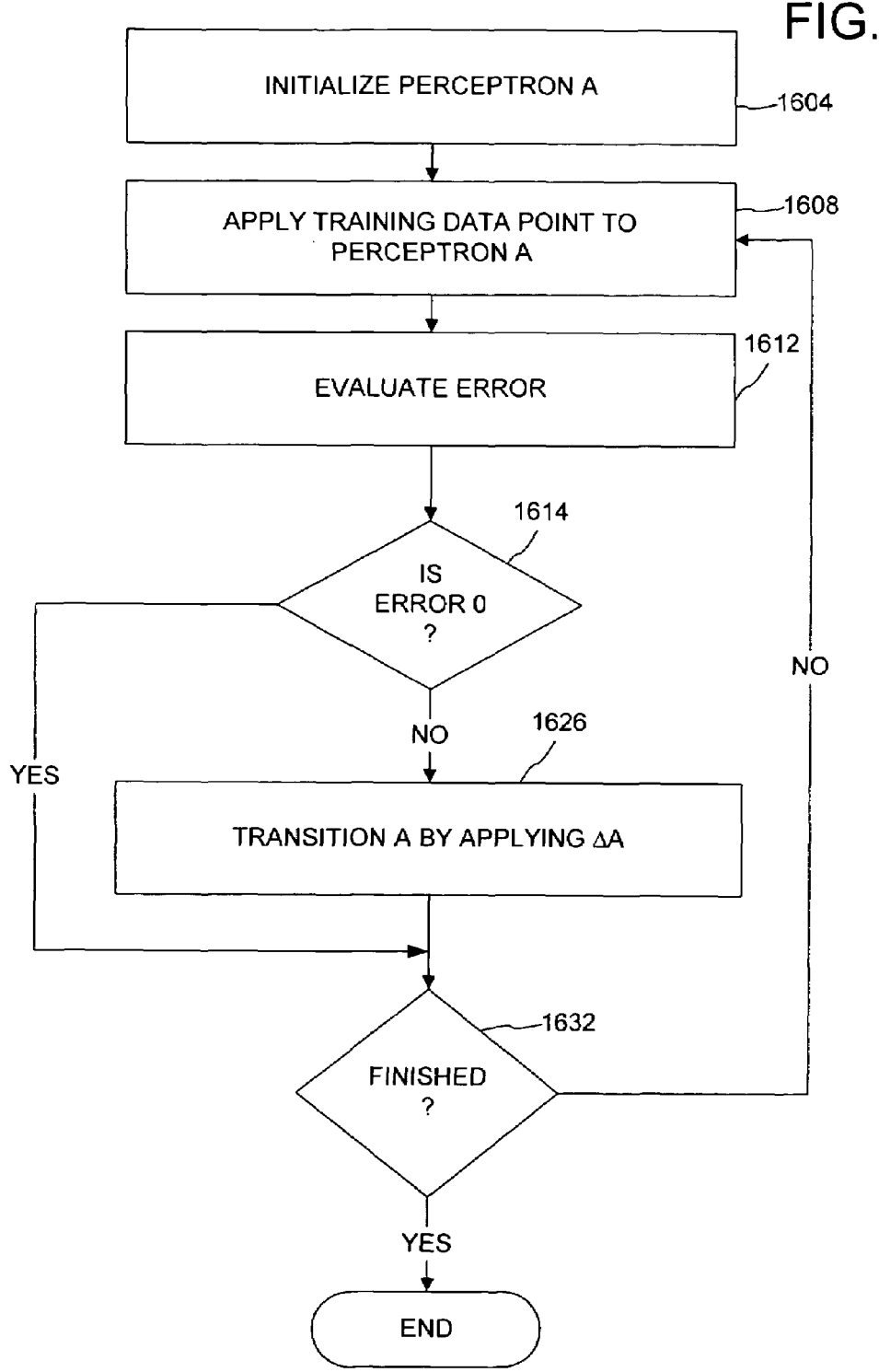
FIG. 16 is a flowchart showing a method for training a perceptron to predict gene expression.

A perceptron is sometimes called a neural network with a single neuron. FIG. 16 illustrates a method for training a perceptron. The perceptron is defined by the coefficient vector $A = (a_1, a_2, \ldots, a_n, b)$ and its output is determined as shown in Equation 1, above. Alternatively, a perceptron is sometimes described as defined by the coefficient vector $A = (a_0, a_1, a_2, \ldots, a_n)$ and having an additional input $X_0$, which is a constant scalar (e.g., 1).

Training is achieved via a training sequence of data of predictive elements and observed values $(X^1, Y^1), (X^2, Y^2) \ldots (X^n, Y^n)$. A variety of techniques can be used to extend a small training set (e.g., the values can be recycled via plural random orderings). In summary, the training set is applied to the perceptron. If the perceptron is in error, the coefficient vector is adjusted.

At 1604, the perceptron is initialized. Initialization can be either random or based on training data. For example, A can be initialized to the cross-covariance vector C between X and Y and the autocorrelation matrix R of $V = (1, X_1, X_2, \ldots, X_m)$. A is thus initialized to $R^+ C$, where $R^+$ is the pseudoinverse of R.

At 1608, a data point in the training data is applied to the perceptron (e.g., a set of observed values for predictive elements are applied and a predicted value is generated based on A).

A variety of training techniques can be used. Generally, a training technique is characterized by the update $$A^{(new)} = A^{(old)} + \Delta A \quad (4)$$

where $\Delta A$ is called a "transition."

At 1612, error is evaluated by comparing the observed value with the predicted value. For example, the training factor can be defined by $$f = (A^{(old)} \cdot V - Y) \quad (5)$$

where V is the vector of predictive inputs and Y is an observed value. The training error is then $$e = f|Y_{pred} - Y| \quad (6)$$

If e is greater than zero, typically the training method attempts to decrease e by appropriately transitioning A. If e is less than zero, the training method attempts to increase e by appropriately transitioning A. An e value of zero implies there is no error, so A is not transitioned. The sign and magnitude of the transition can be determined by f.

An appropriate transition can thus be defined as follows:

$$\Delta A_i = -f \alpha_i (Y - Y_{pred}) X_i \quad (7)$$

where the values $\alpha_i$ are gain factors ($0 < \alpha_i \leq 1$). The gain factors can be advantageously selected for proper training under certain circumstances. Other arrangements can be used (e.g., substituting e for f in the transition or calculating the values in some other order or notation to reach a similar result).

At 1614 if e is zero, $\alpha A_i = 0$ and no transition is necessary, so the method continues at 1632. Otherwise, A is transitioned by applying $\Delta A$ as explained above.

At 1632, it is determined whether training is finished. If not, the method continues at 1608. Any number of stopping criteria can be used, such as testing whether A converges, a fixed number of iterations complete, or a minimum error tolerance is reached.

Alternatively, rather than transitioning A after each data point in the training data set, A can be transitioned after the completion of a cycle of the training data set. For such a technique, e and $\Delta A_i$ can be computed for each data point as above; however, A is updated at the end of each cycle, with $\Delta A$ being the sum of the stepwise increments during the cycle. Similar gain and stopping criteria can be applied.

Testing the Trained Perceptron to Quantify Relatedness

Figure 17:
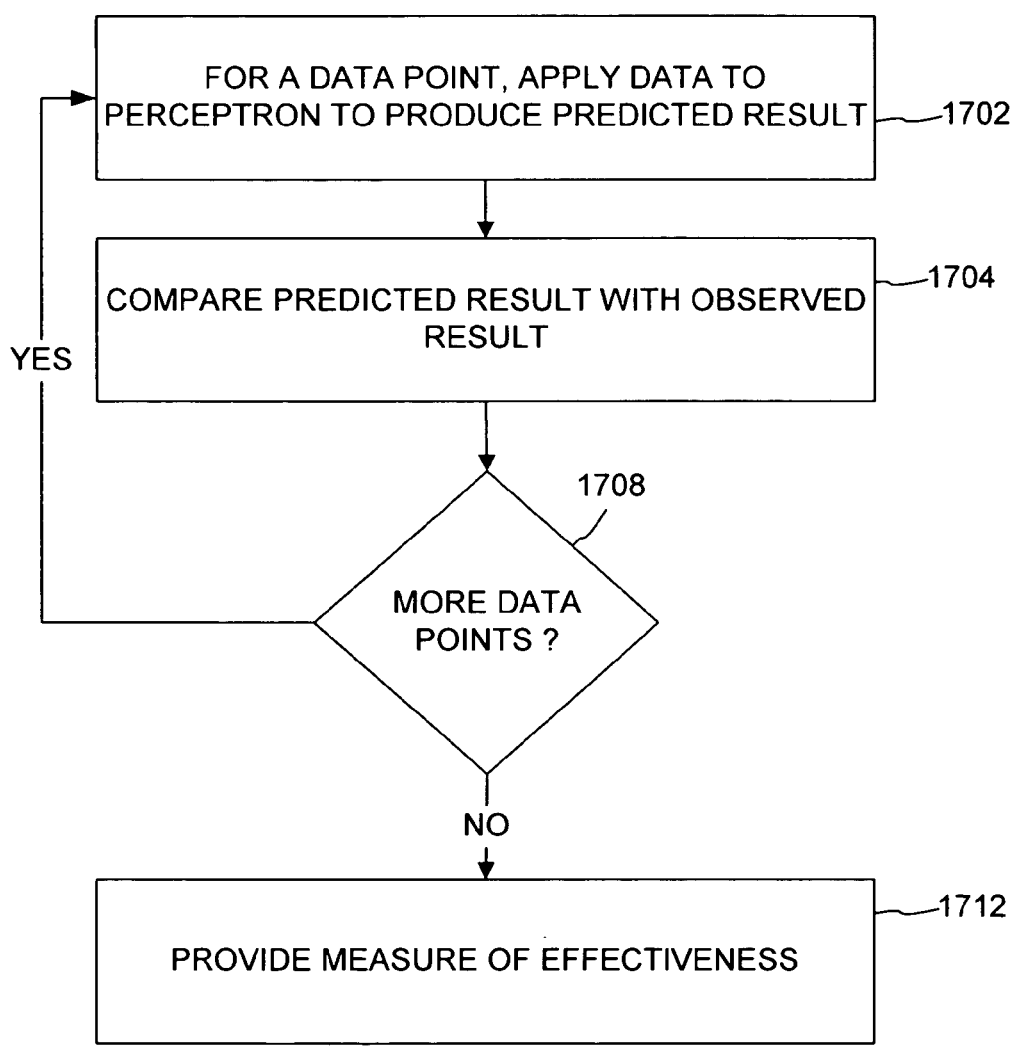
FIG. 17 is a flowchart showing a method for testing the effectiveness of a perceptron in predicting gene expression.

After training is completed, the perceptron can be tested to quantify relatedness of the predictive elements and the predicted gene. A method for testing a perceptron is shown in FIG. 17. At 1702, a data point from the testing data set is applied to the perceptron (i.e., the predictive elements are submitted as inputs to the perceptron) to provide a predicted result, $Y_{pred}$. Then, at 1704 the predicted result is compared with an observed result (e.g., from an experiment observing gene expression). At 1708, if there are more data points, the method continues at 1704. Otherwise, at 1712, a measure of the effectiveness of the perceptron is provided.

Other approaches can be used to provide similar results. For example, the predicted results can be stored and compared as a group to the observed results. An exemplary measure of the effectiveness of the perceptron is a coefficient of determination, which is found by applying Equation 2, above.

Exemplary Combination of Training and Testing of a Perceptron

The above techniques can be applied in a variety of ways. For example, for a set of 30 data points observed, a set of 20 training data sets can be generated (e.g., by randomly reordering, choosing a subset of the observations, or both). Then, for each of the 20 sets of training data, a perceptron is initialized to $R^+C$ and trained on the data. The better of the trained perceptron and the initialized perceptron is then applied to 10 test data sets (e.g., subsets of the observation data that may or may not overlap with the training data) to obtain a measure of the coefficient of determination.

The entire process above can be repeated a large number of times (e.g., 256), and the average of the coefficients of determination is considered to be a quantification of relatedness. In some cases, the perceptron may perform more poorly than a baseline predictor (e.g., the thresholded mean). If so, measurement of the perceptron is considered to be zero.

Moreover, if it is the case that the coefficient of determination for a perceptron is greater when one of the variables is removed, the coefficient of determination is considered to be the greater of the two measurements.

Unconstrained and Constrained Predictors

The theoretically optimal predictor of the target Y is typically unknown and is statistically estimated. The theoretically optimal predictor has minimum error across the population and is designed (estimated) from a sample by a training (estimation) method. The degree to which a designed predictor approximates the optimal predictor depends on the training procedure and the sample size n. Even for a relatively small number of predictive elements, precise design of the optimal predictor typically involves a large number samples. The error, $\epsilon_n$, of a designed estimate of the optimal predictor exceeds the error, $\epsilon_{opt}$, of the optimal predictor. For a large number of experiments, $\epsilon_n$ approximates $\epsilon_{opt}$, but for the small numbers sometimes used in practice, $\epsilon_n$ may substantially exceed $\epsilon_{opt}$. Although gene expression levels for many genes are observed during a typical single microarray experiment, currently only a few samples of biological material are evaluated per microarray.

As the number of system inputs grows, the amount of replicated observations necessary for precise statistical design of an optimal predictor grows more rapidly. Since a designed predictor depends on a randomly drawn sample data set, we use expectations for statistical analysis. Hence, we are concerned with the difference, $E[\epsilon_n]-\epsilon_{opt}$, between the expected error of the designed predictor and the error of the optimal predictor. A small difference means that $E[\epsilon_n]$ provides a good approximation to $\epsilon_{opt}$.

It is sometimes useful to estimate the best predictor from a constrained set of predictors. Since the optimal constrained predictor is chosen from a subset of the possible predictors, its theoretical error exceeds that of the best predictor; however, the best constrained predictor can be designed more precisely from the data. The error, $\epsilon_{con,n}$, an estimate of the optimal constrained predictor exceeds the error, $\epsilon_{opt-con}$, of the optimal constrained predictor. We are concerned with the difference, $E[\epsilon_{con,n}]-\epsilon_{opt-con}$.

If we let $\delta_n = E[\epsilon_n]-\epsilon_{opt}$ and $\delta_{con,n} = E[\epsilon_{con,n}]-\epsilon_{opt-con}$, then the challenges of finding good predictors of gene expression levels are evidently the following: $\epsilon_{opt} \leq \epsilon_{opt-con}$, and $\delta_n \geq \delta_{con,n}$; $\epsilon_{opt}$ is decreased by using more predictive elements, but $\delta_n$ is thereby increased; the stronger the constraint, the more $\delta_{con,n}$ is reduced, but at the cost of increasing $\epsilon_{opt-con}$.

$\delta_n$ and $\delta_{con,n}$ are the costs of design in the unconstrained and constrained settings, respectively. If we have access to an unlimited number of experiments (and the design procedures do not themselves introduce error), then we could make both $\delta_n$ and $\delta_{con,n}$ arbitrarily small and have $$\epsilon_n \approx \epsilon_{opt} \leq \epsilon_{opt-con} \approx \epsilon_{con.n} \tag{8}$$

However, with a low number of experiments, $\delta_n$ can significantly exceed $\delta_{con,n}$. Thus, the error of the designed constrained predictor can be smaller than that of the designed unconstrained predictor.

Figure 18:
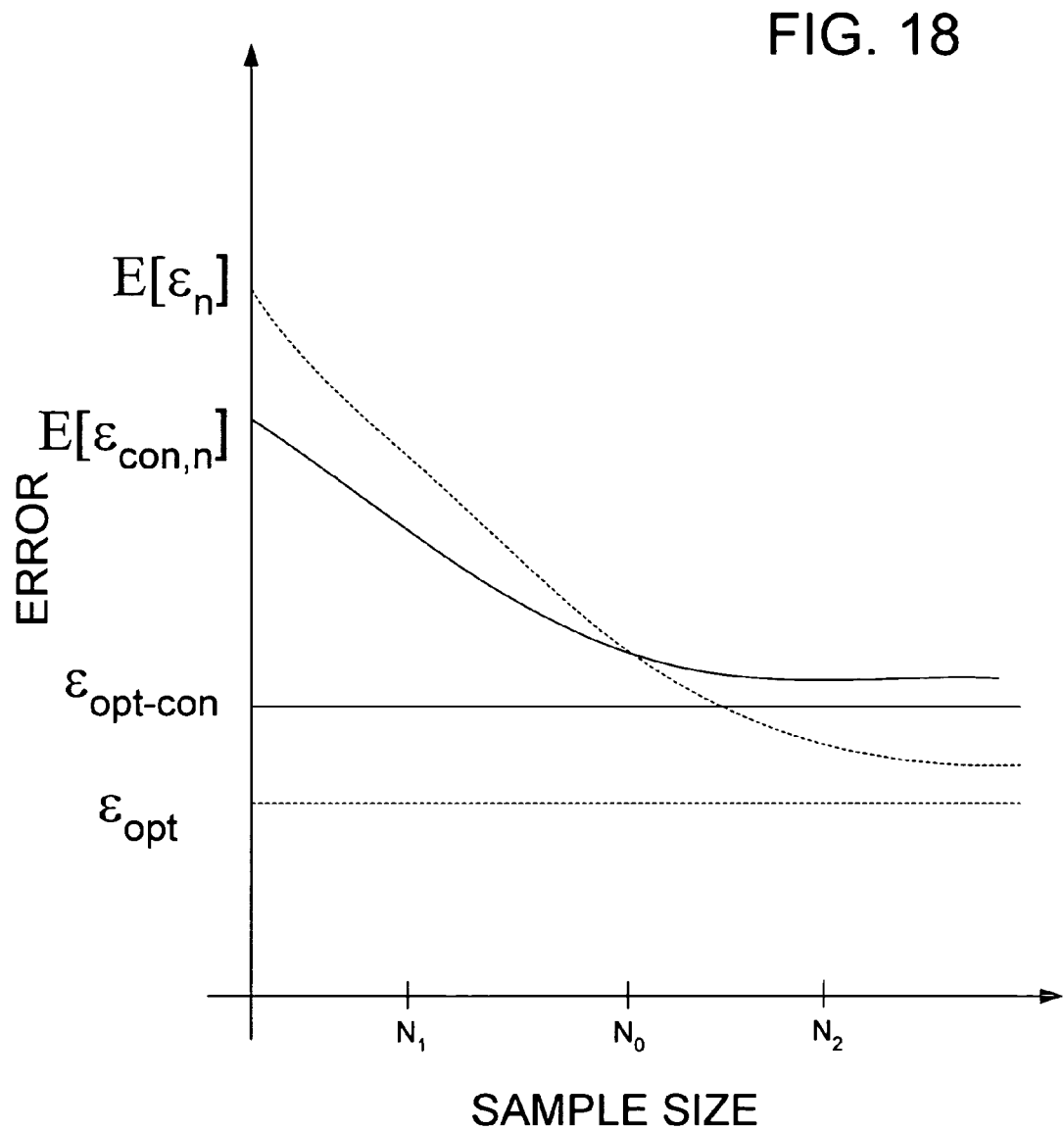
FIG. 18 is a graph denoting error of unconstrained and constrained predictors.

FIG. 18 illustrates the phenomenon by comparing error of unconstrained and constrained predictors. The axes correspond to sample size n and error. The horizontal dashed and solid lines represent $\epsilon_{opt}$ and $\epsilon_{opt-con}$, respectively. The decreasing dashed and solid lines represent $E[\epsilon_n]$ and $E[\epsilon_{con,n}]$ respectively. If n is sufficiently large (e.g., $N_2$), then $E[\epsilon_n]<E[\epsilon_{con,n}]$; however, if n is sufficiently small (e.g., $N_2$), then $E[\epsilon_n]>E[\epsilon_{con,n}]$. The point $N_0$ at which the decreasing lines cross is the cut-off: for $n>N_0$, the constraint is detrimental; for $n<N_0$, the constraint is beneficial. When $n<N_0$, the advantage of the constraint is measured by the difference between the decreasing solid and dashed lines.

Even if a designed constrained predictor does not perform well, the truly optimal constrained predictor may still perform well. Moreover, a less constrained predictor might provide good prediction had we a sufficient number of experiments to design it. A constraint will typically err by missing a relationship, not erroneously indicating a strong relationship, thereby avoiding falsely attributing a predictive relation where none exists. The relationships missed depend on the constraint. Sometimes a system can be modeled in such a way that a constraint can be derived that does not yield increased error; however, this is not typical in nonlinear settings.

Training and Testing Data Sets

In a mathematical sense, gene relatedness can be quantified by a measure of the coefficient of determination of an optimal predictor for a set of variables under ideal observation conditions, where the coefficient of determination is the relative decrease in error owing to the presence of the observed variables.

$$\theta_{opt} = (\epsilon_o - \epsilon_{opt})/\epsilon_o \qquad (9)$$

where $\epsilon_o$ is the error for the best predictor in the absence of observations. Since $\epsilon_{opt} \leq \epsilon_o$, $0 \leq \theta_{opt} \leq 1$. A similar definition applies for constrained predictors. So long as the constraint allows all constant predictors, $0 \leq \theta_{opt-con} \leq 1$.

For the unconstrained ternary predictor, $$\theta_{opt} = (\epsilon_\mu - \epsilon_{opt})/\epsilon_\mu \qquad (10)$$

where $\epsilon_\mu$ is the mean square error from predicting Y by applying $T(\mu_Y)$, the ternary threshold of the mean of Y. For constrained predictors, $\epsilon_{opt}$ is replaced by $\epsilon_{opt-con}$ to obtain $\theta_{opt-con}$, and $\theta_{opt-con} \leq \theta_{opt}$.

For designed predictors, in Equation 10, $\epsilon_\mu$ is replaced by $\epsilon_{\mu,n}$ to give $$\theta_n = (\epsilon_{\mu,n} - \epsilon_n)/\epsilon_{\mu,n} \qquad (11)$$

$E[\theta_n]$, the expected sample coefficient of determination, is found by taking expected values on both sides of Equation 11. $E[\epsilon_n] \geq \epsilon_{opt}$, and typically $E[\epsilon_n] > \epsilon_{opt}$, where the inequality can be substantial for small samples. Unless n is quite small, it is not unreasonable to assume that $\epsilon_{\mu,n}$ precisely estimates $\epsilon_\mu$, since estimation of $\mu_Y$ does not require a large sample. Under this assumption, if we set $\epsilon_{\mu,n} = \epsilon_\mu$ in Equation 11 and take expectations, we obtain $$E[\theta_n] \approx (\epsilon_{\mu,n} - E[\epsilon_n])/\epsilon_{\mu,n} \qquad (12)$$

Because $E[\epsilon_n] > \epsilon_{opt}$, Equations 10 and 12 yield $E[\epsilon_n] < \theta_{opt}$ and $\theta_n$ is a low-biased estimator of $\theta_{opt}$.

For a constrained optimization, $\epsilon_n$ is replaced by $\epsilon_{con.n}$ to obtain $\epsilon_{con.n}$. In analogy to Equation 8, if there is a sufficient number of experiments, then $$\theta_{con.n} \approx \theta_{opt-con} \leq \theta_{opt} \approx \theta_n \qquad (13)$$

As the number of samples increases, the approximations get better. In a low sample environment, it is not uncommon to have $E[\theta_{con.n}] > E[\theta_n]$.

Data is used to estimate $\theta_n$ and design predictors. A limited sample size presents a challenge. For unconstrained predictors (and analogously for constrained predictors), one can use the resubstitution estimate, $\ddot{\theta}_n$. For resubstitution, data is uniformly treated as training data to train (or design) the best predictor, estimates of $\epsilon_{\mu,n}$ and $\epsilon_n$ are obtained by applying the thresholded estimated mean and the designed predictor to the training data, and $\ddot{\theta}_n$ is then computed by putting these estimates into Equation 11. In other words, the same data can be used to train and test. $\ddot{\theta}_n$ estimates $\theta_n$ and thereby serves as an estimator of $\theta_{opt}$. The resubstitution estimate can be expected to be optimistic, meaning it is biased high.

A different approach is to split the data into training and test data, thereby producing cross-validation. A predictor is designed from the training data, estimates of $\epsilon_{\mu,n}$ and $\epsilon_n$ are obtained from the training data, and an estimate of $\theta_n$ is computed by putting the error estimates into Equation 11. Since this error depends on the split, the procedure is repeated a number of times (e.g., with different splits) and an estimate, $\hat{\theta}_n$, is obtained by averaging. For random sampling, the estimates of $\epsilon_{\mu,n}$ and $\epsilon_n$ are unbiased, and therefore the quotient of Equation 11 will be essentially (close to being) unbiased as an estimator of $\theta_n$. Since $\theta_n$ is a pessimistic (low-biased) estimator of $\theta_{opt}$, $\hat{\theta}_n$ is a pessimistic estimator of $\theta_{opt}$.

Another issue is the number of predictor variables. For m and r predictor variables, m<r, if $\epsilon_{opt}(m)$ denotes the error for the m-variable predictor, then $\epsilon_{opt}(r) \leq \epsilon_{opt}(m)$. Prediction error decreases with an increasing number of variables. Hence, $\theta_{opt}(r) \geq \theta_{opt}(m)$. However, with an increasing number of variables comes an increase in the cost of estimation (the difference between the errors of the designed and optimal predictors.) Intuitively, the information added by expanding the number of predictor variables becomes ever more redundant, thereby lessening the incremental predictive capability being added, whereas the inherent statistical variability in the new variables increases the cost (error) of design. Letting $\delta_n(m) = E[\epsilon_n(m)] - \epsilon_{opt}(m)$, we have $\delta_n(m) \leq \delta_n(r)$, and it may happen that $\epsilon_n(r) > \epsilon_n(m)$ and $\theta_n(r) < \theta_n(m)$. Since $\theta_{opt}(r) \geq \theta_{opt}(m)$, we choose the maximum between $\hat{\theta}_n(r)$ and $\hat{\theta}_n(m)$ as our estimator of $\theta_{opt}(r)$.

Cross validation is beneficial because $\hat{\theta}_n$ gives a conservative estimate of $\theta_{opt}$. Thus, we do not obtain an overly optimistic view of the determination. On the other hand, training and testing with the same data provides a large computational savings. This is important when searching over large combinations of predictor and target genes.

Under the current scenarios, the goal is typically to compare coefficients of determination to find sets that appear promising. In one case, comparison is between high-biased values; in another, comparison is between low-biased values.

Exemplary Gene Expression Data Analysis to Quantify Gene Relatedness

The following example demonstrates the ability of the full-logic and perceptron predictors to detect relationships based on changes of transcript level in response to genotoxic stresses.

As a result of a microarray study surveying transcription of 1238 genes during the response of a myeloid line to ionizing radiation (see Amundson et al., "Fluorescent cDNA Microarray Hybridization Reveals Complexity and Heterogeneity of Cellular Genotoxic Stress Responses," *Oncogene* 18, 3666–3672, 1999), 30 genes not previously known to participate in response to ionizing radiation ("IR") were found to be so responsive. The responsiveness of a subset of nine of these genes was examined by blot assays in 12 cell lines stimulated with IR, a chemical mutagen methyl methane sulfonate ("MMS"), or ultraviolet radiation ("UV"). The cell lines were chosen so a sampling of both p53 proficient and p53 deficient cells would be assayed.

Table 4 shows data indicating observed gene expression levels for the various genes. The condition variables IR, MMS, and UV have values 1 or 0, depending on whether the condition is or is not in effect. Gene expression is based on comparisons to the same cell line not exposed to the experimental condition. −1 means expression was observed to go down, relative to untreated; 0 means unchanged; and +1 means expression was observed to go up.

To validate the analysis, data for two fictitious genes ("AHA" and "OHO") were generated. Gene expression rules for the fictitious genes were created, making expression of the fictitious genes dependent on other gene expression levels in the set. However, the concordance of the generated data with the rules was varied (i.e., the rules were not strictly adhered to).

For gene AHA, a rule states AHA is up-regulated if p53 is up-regulated, but down-regulated if RCH1 and p53 are down-regulated. Full concordance with the rule would have produced 15 instances of up-regulation and 5 instances of down-regulation; the data generated includes 13 of the 15 up-regulations and all of the down-regulations.

For gene OHO, a rule states OHO is up-regulated if MDM2 is up-regulated and RCH1 is down-regulated; OHO is down-regulated if p53 is down-regulated and REL-B is up-regulated. Full concordance with this rule would have produced 4 up-regulations and 5 down-regulations. The data generated has the 4 up-regulations, plus 7 others, and only 2 of the 5 down-regulations.

The data show the genes in the survey are not uniformly regulated in the various cell types. The genes showed up- or down-regulation in at least one cell type; however, the number of changes observed across the lines varies. Such a varied response reflects the different ways in which different cells respond to the same external stimuli based on their own internal states. The data are therefore a useful test of the predictors. Since predictors operate by rules relating changes in one gene with changes in others, predictors were not created to predict expression of genes exhibiting fewer than four changes in the set of 30 observations. MBP1 and SSAT were thus eliminated as predicted genes.

For the fictitious genes, the designed predictors identified both the p53 and RCH1 components of the transcription rule set for AHA. For instance, using the perceptron and splitting the training data set from the test data set, a 0.785 estimate of the coefficient of determination was given. This value is biased low because splitting the data results in cross-validation. Since many rule violations were introduced into the data set for the OHO gene, it was expected that the coefficient of determination would not be high when using the predictors MDM2, RCH1, p53, and REL-B; this expectation was met.

TABLE 4

Gene Expression Observations

| | | Genes | | | | | | |
|---|---|---|---|---|---|---|---|---|
| Cell line | Cond. | RCH1 | BCL3 | FRA1 | REL-B | ATF3 | IAP-1 | PC-1 |
| 1 ML-1 | I | −1 | 1 | 1 | 1 | 1 | 1 | 1 |
| 2 ML-1 | M | 0 | 0 | 0 | 0 | 1 | 0 | 0 |
| 3 Molt4 | I | −1 | 0 | 0 | 1 | 1 | 0 | 1 |
| 4 Molt4 | M | 0 | 0 | 1 | 0 | 1 | 0 | 0 |
| 5 SR | I | −1 | 0 | 0 | 1 | 1 | 1 | 1 |
| 6 SR | M | 0 | 0 | 0 | 0 | 1 | 0 | 0 |
| 7 A549 | I | 0 | 0 | 0 | 0 | 0 | 0 | 0 |
| 8 A549 | M | 0 | 0 | 0 | 0 | 1 | 0 | 0 |
| 9 A549 | U | 0 | 0 | 0 | 0 | 1 | 0 | 0 |
| 10 MCF7 | I | −1 | 0 | 1 | 1 | 0 | 0 | 0 |
| 11 MCF7 | M | 0 | 0 | 1 | 0 | 1 | 0 | 0 |
| 12 MCF7 | U | 0 | 0 | 1 | 1 | 1 | 0 | 0 |
| 13 RKO | I | 0 | 1 | 0 | 1 | 1 | 1 | 1 |
| 14 RKO | M | 0 | 0 | 0 | 0 | 1 | 0 | 0 |
| 15 RKO | U | 0 | 0 | 0 | 0 | 1 | 0 | 0 |
| 16 CCRF-CEM | I | −1 | 1 | 1 | 1 | 1 | 0 | 1 |
| 17 CCRF-CEM | M | 0 | 0 | 0 | 0 | 1 | 0 | 0 |
| 18 HL60 | I | −1 | 1 | 0 | 1 | 1 | 0 | 1 |
| 19 HL60 | M | 0 | 0 | 1 | 0 | 1 | 0 | 0 |
| 20 K562 | I | 0 | 0 | 0 | 0 | 0 | 0 | 0 |
| 21 K562 | M | 0 | 0 | 0 | 0 | 1 | 0 | 0 |
| 22 H1299 | I | 0 | 0 | 0 | 1 | 0 | 0 | 1 |
| 23 H1299 | M | 0 | 0 | 0 | 0 | 1 | 0 | 0 |
| 24 H1299 | U | 0 | 0 | 0 | 0 | 1 | 0 | 1 |
| 25 RKO/E6 | I | −1 | 1 | 0 | 1 | 0 | 1 | 1 |
| 26 RKO/E6 | M | −1 | 0 | 0 | 0 | 1 | 0 | 0 |
| 27 RKO/E6 | U | −1 | 0 | 0 | 0 | 1 | 0 | 0 |
| 28 T47D | I | 0 | 0 | 0 | 1 | 0 | 0 | 0 |
| 29 T47D | M | 0 | 0 | 0 | 0 | 1 | 0 | 0 |
| 30 T47D | U | 0 | 0 | 0 | 0 | 1 | 0 | 0 |

| | Genes | | | | | | Cond. | | |
|---|---|---|---|---|---|---|---|---|---|
| Cell line | MBP-1 | SSAT | MDM2 | p21 | p53 | AHA | OHO | IR | MMS | UV |
| 1 ML-1 | 1 | 1 | 1 | 1 | 1 | 1 | 1 | 1 | 0 | 0 |
| 2 ML-1 | 0 | 0 | 1 | 1 | 1 | 1 | 0 | 0 | 1 | 0 |
| 3 Molt4 | 0 | 0 | 1 | 1 | 1 | 1 | 1 | 1 | 0 | 0 |
| 4 Molt4 | 0 | 0 | 0 | 1 | 1 | 1 | 0 | 0 | 1 | 0 |
| 5 SR | 1 | 0 | 1 | 1 | 1 | 1 | 1 | 1 | 0 | 0 |
| 6 SR | 0 | 0 | 1 | 1 | 1 | 1 | 0 | 0 | 1 | 0 |
| 7 A549 | 0 | 0 | 1 | 1 | 1 | 0 | 0 | 1 | 0 | 0 |
| 8 A549 | 0 | 0 | 0 | 1 | 1 | 1 | 0 | 0 | 1 | 0 |
| 9 A549 | 0 | 0 | 0 | 1 | 1 | 1 | 0 | 0 | 0 | 1 |
| 10 MCF7 | 0 | 0 | 1 | 1 | 1 | 0 | 1 | 1 | 0 | 0 |

TABLE 4-continued

Gene Expression Observations

| 11 | MCF7 | 0 | 0 | 1 | 1 | 1 | 1 | 0 | 0 | 1 | 0 |
|----|------|---|---|---|---|---|---|---|---|---|---|
| 12 | MCF7 | 0 | 0 | 1 | 1 | 1 | 1 | 0 | 0 | 0 | 1 |
| 13 | RKO | 0 | 0 | 1 | 1 | 1 | 1 | 0 | 1 | 0 | 0 |
| 14 | RKO | 0 | 0 | 0 | 1 | 1 | 1 | 0 | 0 | 1 | 0 |
| 15 | RKO | 0 | 0 | 0 | 1 | 1 | 1 | 0 | 0 | 0 | 1 |
| 16 | CCRF-CEM | 0 | 0 | 0 | 0 | −1 | −1 | 0 | 1 | 0 | 0 |
| 17 | CCRF-CEM | 0 | 0 | 0 | 0 | −1 | 0 | 0 | 0 | 1 | 0 |
| 18 | HL60 | 0 | 1 | 0 | 1 | −1 | −1 | −1 | 1 | 0 | 0 |
| 19 | HL60 | 0 | 0 | 1 | 1 | −1 | 0 | 1 | 0 | 1 | 0 |
| 20 | K562 | 0 | 0 | 0 | 0 | −1 | 0 | 0 | 0 | 1 | 0 |
| 21 | K562 | 0 | 0 | 0 | 0 | −1 | 0 | 0 | 0 | 1 | 0 |
| 22 | H1299 | 0 | 0 | 0 | 0 | −1 | 0 | 0 | 1 | 0 | 0 |
| 23 | H1299 | 0 | 0 | 0 | 1 | −1 | 0 | 1 | 0 | 1 | 0 |
| 24 | H1299 | 0 | 0 | 0 | 1 | −1 | 0 | 1 | 0 | 0 | 1 |
| 25 | RKO/E6 | 0 | 0 | 0 | 0 | −1 | −1 | 0 | 1 | 0 | 0 |
| 26 | RKO/E6 | 0 | 0 | 0 | 1 | −1 | −1 | 1 | 0 | 1 | 0 |
| 27 | RKO/E6 | 0 | 0 | 0 | 1 | −1 | −1 | 1 | 0 | 0 | 1 |
| 28 | T47D | 0 | 0 | 0 | 1 | −1 | 0 | −1 | 1 | 0 | 0 |
| 29 | T47D | 0 | 0 | 0 | 1 | −1 | 0 | 1 | 0 | 1 | 0 |
| 30 | T47D | 0 | 0 | 0 | 1 | −1 | 0 | 1 | 0 | 0 | 1 |

The coefficient of determination calculations can be presented as arrow plots of prediction trees, as shown in FIG. 19. The predicted gene (sometimes called a "target" gene) is shown to the right and the chained predictors to the left. The coefficient of determination that results when adjoining a predictive element is placed to the right of the predictive element. For example, in FIG. 19, Predictor 1 achieves a coefficient of determination of $\theta_1$. Using Predictors 1 and 2 together achieves $\theta_2$, and using Predictors 1, 2, and 3 together achieves $\theta_3$.

The analysis agrees with expectations provided by existing biological information. For example, it is expected that MDM2 is incompletely, but strongly predicted by p53. As shown in FIG. 20A, this expectation was met. Additions of further genes to p53 do not increase the accuracy of the prediction. Similarly, since it is known that p53 is influential, but not determinative of the up-regulation of both p21 and MDM2, some level of prediction of p53 should be possible by a combination of these two genes. As shown in FIG. 20B, this expectation was also met. Moreover, as p21 shows both p53 dependent and p53 independent regulation in response to genomic damage (see Gorospe et al., "Up-regulation and Function Role of p21 Wafl/Cip1 During Growth Arrest of Human Breast Carcinoma MCF-7 Cells by Phenyacetate," Cell Growth Differ 7, 1609–15, 1996), it was expected that the p53 component would not be recognized by the analysis. As shown in FIG. 20C, two other genes (MDM2 and ATF3) were chosen over p53 as better predictive elements.

Among the newly-found IR responsive genes (FRA1, ATF3, REL-B, RCH1, PC 1, IAP-1, and MBP-1), a set of relationships is seen that appears to link the behaviors of REL-B, RCH1, PC-1, MBP-1, BCL2, IAP-1, and SSAT. Sets of full-logic prediction trees for REL-B, PC-1, RCH1, and IAP-1 are shown in FIGS. 21A–D; perceptron versions appear at FIGS. 22A–D. Both a full-logic and perceptron analyses find a variety of apparently significant similarities of expression behavior within this set. Some of these genes also show a high degree of predictability based solely on exposure to ionizing radiation. When these genes are viewed with an eye to IR responsiveness, it becomes apparent they share an overall trend to show expression level changes in response to IR rather than to UV or MMS. Even though MBP1 and SSAT only responded to IR at the very low rate of 17% of the possible changes, they responded only to this stimulus and not to the other genotoxic stimuli, and were thus associated with other genes showing similar response. This example illustrates the power of the analyses to find new, potentially significant relations.

Using data splitting, the error relation between the full-logic and perceptron predictors is illustrated. Using cross-validation, the estimated coefficients of determination of the best full-logic and perceptron predictors of BCL3 in terms of IAP-1, PC-1 and SSAT are 0.334 and 0.461, respectively. Since the estimate by the perceptron exceeds that by the full-logic version, the optimal full-logic predictor has a coefficient of determination greater than 0.461. This is true because the error of the optimal predictor is less than or equal to that of a constrained predictor. In fact, it could be that the optimal full-logic predictor is a perceptron, but this is not determined from the limited data available.

For prediction of BCL3 in terms of RCH1, SSAT, and p21, the best full-logic and perceptron predictors (using cross validation) estimate the coefficient of determination at 0.652 and 0.431, respectively. Constraining prediction to a perceptron underestimates the degree to which BCL3 can be predicted by RCH1, SSAT, and p21. In fact, the true coefficient of determination for the optimal full-logic predictor is likely to be significantly greater than 0.652. Moreover, performance of the optimal full-logic predictor almost surely exceeds that of the optimal perceptron by more than the differential 0.221, but this cannot be quantified from the data. However, it can be concluded with confidence that the substantial superior performance of the full-logic predictor shows the relation between RCH1, SSAT, and p21 (as predictive elements) and BCL3 (as predicted gene) is strongly nonlinear.

The different ways in which full-logic and perceptron predictors operate to find relationships can be illustrated by examining the prediction each makes for the target gene BCL3. The prediction trees of FIGS. 23A and 23B illustrate the optimal gene sets chosen by a perceptron method and full-logic method, respectively. FIG. 23C shows the perceptron-based method's quantification for the genes selected by the full-logic version, and FIG. 23D shows the full-logic method's quantification for the genes selected by the perceptron version. Each approach imposes different computation constraints on input measurements.

Exemplary User Interface

Various user interface features are provided to enable users to more easily navigate and analyze the data generated via the techniques described above.

For example, the results of an analysis can be computed and stored into tables (e.g., one for each predicted gene) for access by a user. So that a user can more easily peruse the tables, various table-manipulating features are provided.

A user can specify a range n–m for a table, and the sets of predictive elements ranked (based on coefficient of determination) n through m are shown, and the user can scroll through the results. A gene can be specified as "required," in which case only sets of predictive elements containing the specified gene are displayed.

One can limit the number of times a gene or gene set appears in the table to omit combinations containing a particular gene. This can be useful, for example, because adding further genes to the set simply increases the coefficient of determination.

One can specify an incremental threshold. Then, only those predictor sets for which there is an increase greater than or equal to the incremental threshold when a gene has been added are shown. This can be useful, for example, in identifying situations in which adjoining a gene to a gene set yields a significant increase in the coefficient of determination.

One can delete from a table any gene with an expression level that did not change some minimal number of times across the experiments, and the user can issue a query for data regarding a specific target and predictor set.

Figure 24:
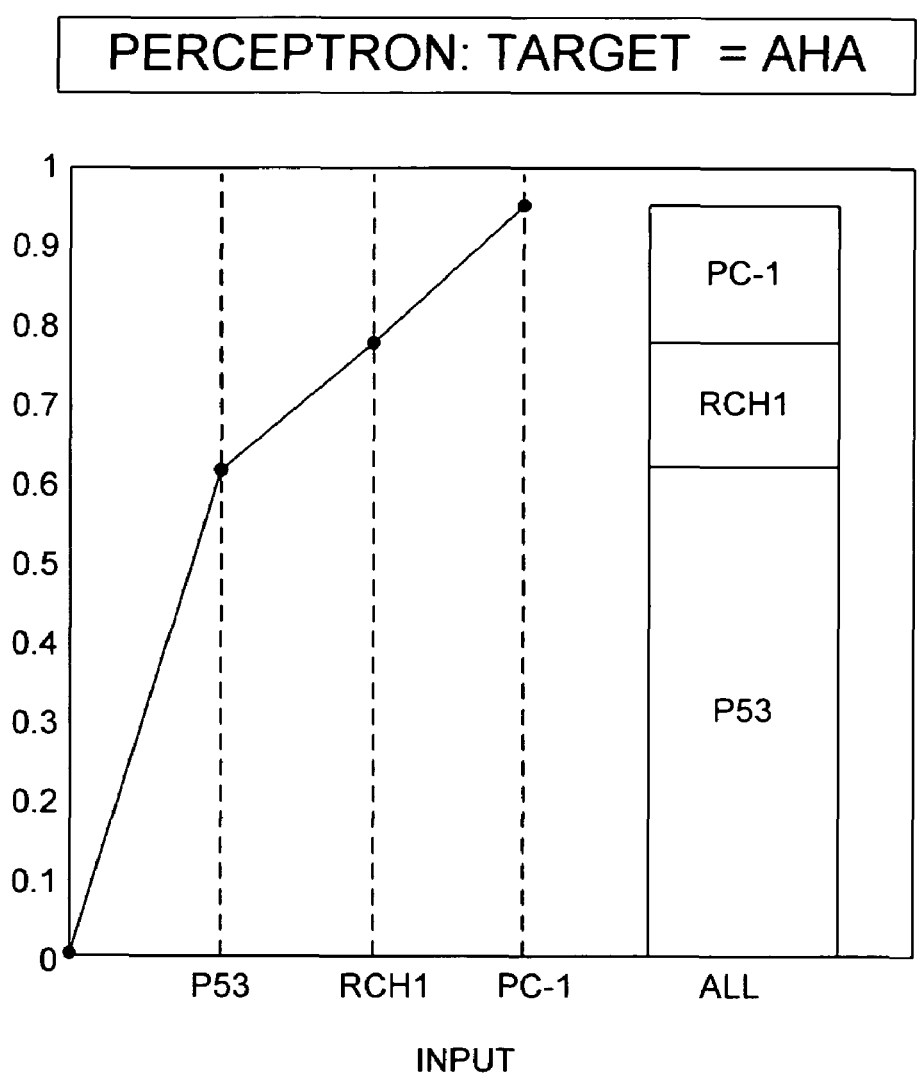
FIG. 24 is a screen capture of a graph showing increases in the coefficient of determination resulting from addition of predictive elements.

In addition, the results can be reviewed as part of a helpful graphical user interface. For example, for any set of predictive elements and a predicted gene, a graph can be plotted to show the increase in coefficient of determination as the set of predictive elements grows. The order of inclusion of the predictive elements can be specified, or the graph can automatically display the best single predictive element first, and given that element, the next best two are shown next, and so forth. An example for gene AHA based on the data of Table 4 is shown in FIG. 24.

In addition to showing the performance of a single set of predictive elements for a predicted gene, the software allows visualization for plural sets for a given predicted gene or for more than one predicted gene.

Figure 25:
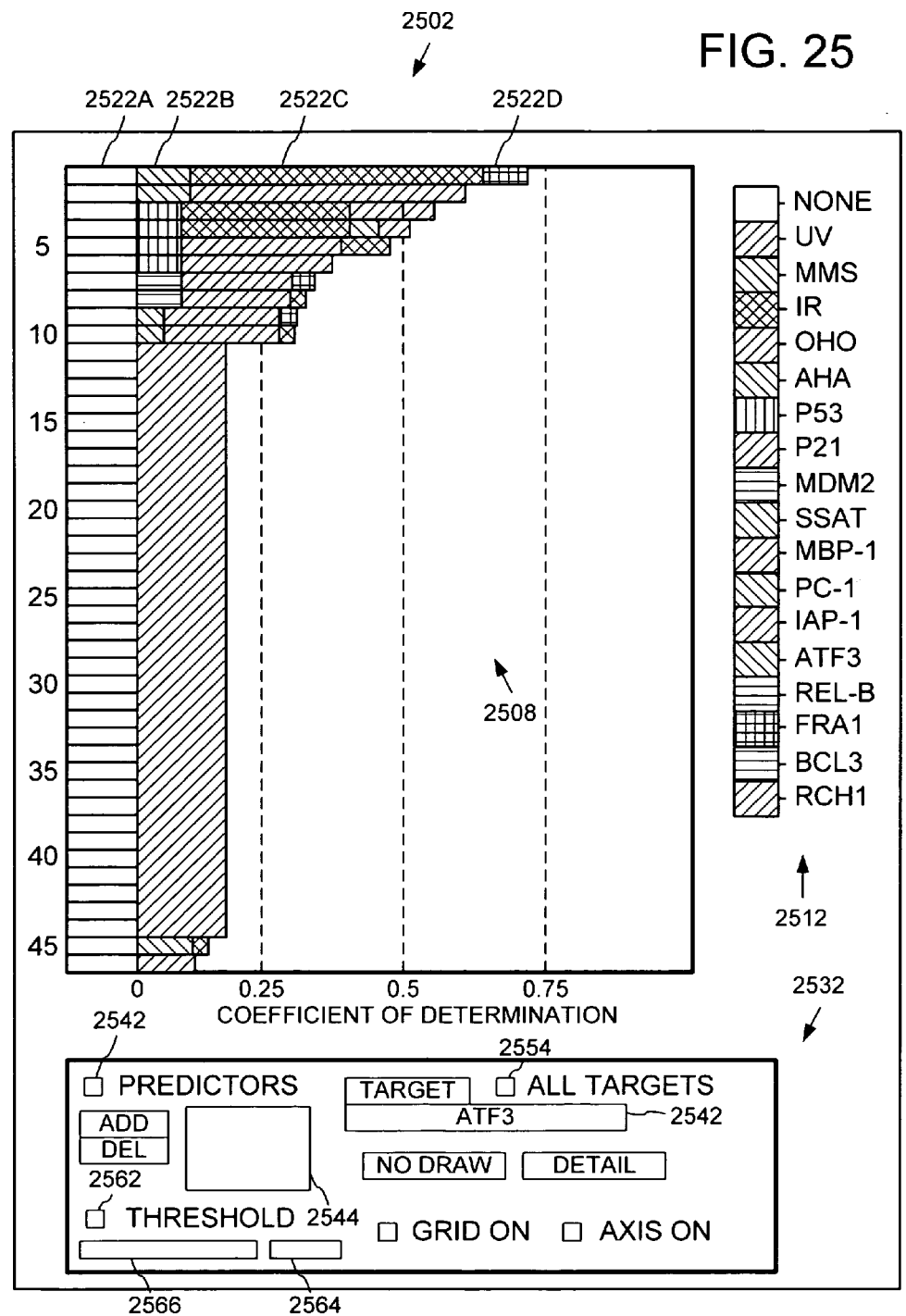
FIG. 25 is a screen capture showing a user interface presenting plural sets of predictive elements for a particular predicted gene.

FIG. 25 shows an exemplary user interface for presenting plural sets of predictive elements for a particular predicted gene, ATF3. Typically, redundancies are automatically removed. In an actual analysis of the data shown in Table 4, 80 sets of predictive elements were found after redundancies were removed. For the sake of brevity, FIG. 25 shows only some of the predictive elements in the form presented by a user interface.

Within the display region 2502, bars 2508 representing predictive elements are shown. A legend 2512 denotes a color for the predictive elements and predicted genes shown. To assist in interpretation, colors in the legend are typically chosen in order along the frequency of visible light (i.e., the colors appear as a rainbow). Further, the bars are ordered by size (e.g., longer bars are at the top). As a result, genes most likely to be related to the target gene are presented at the top.

For example, bar 2522 represents a coefficient of determination value slightly less than 0.75. The predicted gene and contributors to the coefficient are denoted by bar segments 2522A–2522D. 2522A is of fixed length and is of a color representing the predicted gene (ATF3). The bar segment 2522B is of a length and appropriate color indicating contribution by a predictive element (PC-1). The bar segments 2522C–D similarly indicate contributions by IR and FRA1, respectively, and are also of a color according to the legend 2512.

The user can specify which bar segments are to be displayed via the controls 2532. By checking the predictors checkbox 2542, the display is limited to those bar segments having the predictors listed in the box 2544. Predictors can be added and deleted from the box 2544.

The user can limit the display to a particular predicted gene specified in the target gene box 2552 or display bars for all targets by clicking the "all targets" checkbox 2554. For the sake of completeness, conditions such as IR are included as targets in the display.

Further, the user can specify a threshold by checking the threshold checkbox 2562 and specifying a value in the threshold box 2564. The threshold slider 2566 allows another way to specify or modify a threshold. Specifying a threshold limits the display to those bars having a total coefficient of determination at least as high as the threshold specified. To assist in visual presentation, the bars can grow or shrink in height depending on how many are presented. For example, if very few bars are presented, they become taller and the colors are thus more easily distinguishable on the display.

When bars for plural targets are displayed, the bars can be ordered based on predicted gene first and length second. For example, the set of bars relating to a first particular predicted gene are presented in order of length at the top, followed underneath by a set of bars relating to a second particular predicted gene in order of length, and so forth. If the predicted genes are ordered according to the corresponding color's frequency, the bar segments representing the predicted genes (e.g., 2522A) can be ordered to produce a rainbow effect. Such a presentation assists in differentiation of the colors and identification within the legend. This is sometimes helpful because a presentation of plural targets tends to have very many bars, which can visually overwhelm the user.

Figure 26:
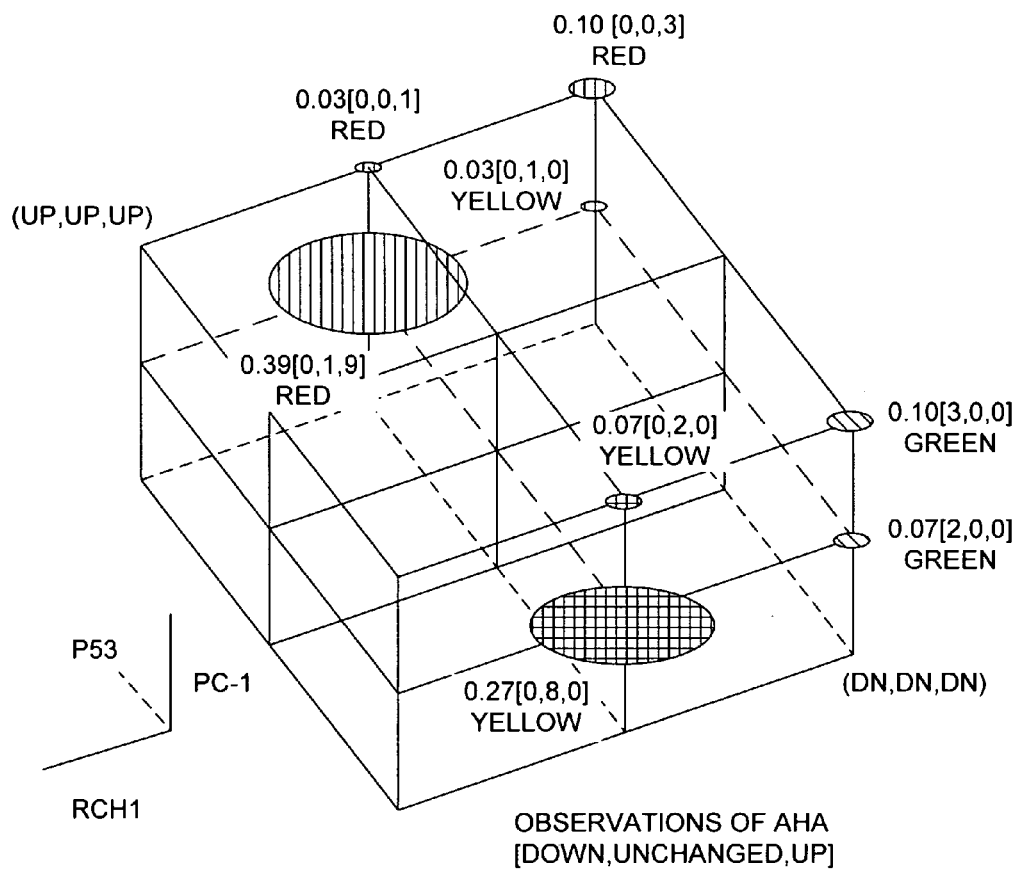
FIG. 26 is a screen capture showing a cubical representation of data for a particular set of predictive elements and a predicted gene AHA.

In the case of a predictive element set of size three, a cubical graph can portray the observed data for each predictive element For example, FIG. 26 shows data observed for the PC-1, RCH1, and p53, which were used to predict the fictitious gene AHA. The presence and size of spheres appearing at various coordinates indicate the number of observations for a particular triple in the data of Table 4. Although the spheres are shown in black and white in the drawing, in an implementation, the color of the sphere indicates whether expression of AHA was up-regulated (red), unchanged (yellow), or down-regulated (green). The percentage of observations falling within the triple is also displayed.

For example, sphere 2622 indicates that a particular triple (PC-1=+1, RCH1=−1, and p53=−1) was observed three times. The values in parentheses indicate the number of times down-regulation, unchanged, or up-regulation were observed, respectively, for this triple (3 down-regulations were observed). The sphere is green because most (i.e., all 3) of the observations were down-regulations. 10% of the total observations relating to the AHA gene were of the triple (+1, −1, −1), so "0.10" is displayed proximate the sphere.

The cubical graph shows the degree to which the target values tend to separate the predictive elements. Actual counts are also shown, along with the fraction of time a triple appears in the observations. The cubical graph can be rotated and viewed from different angles. An object other than a sphere can be used.

Figure 27:
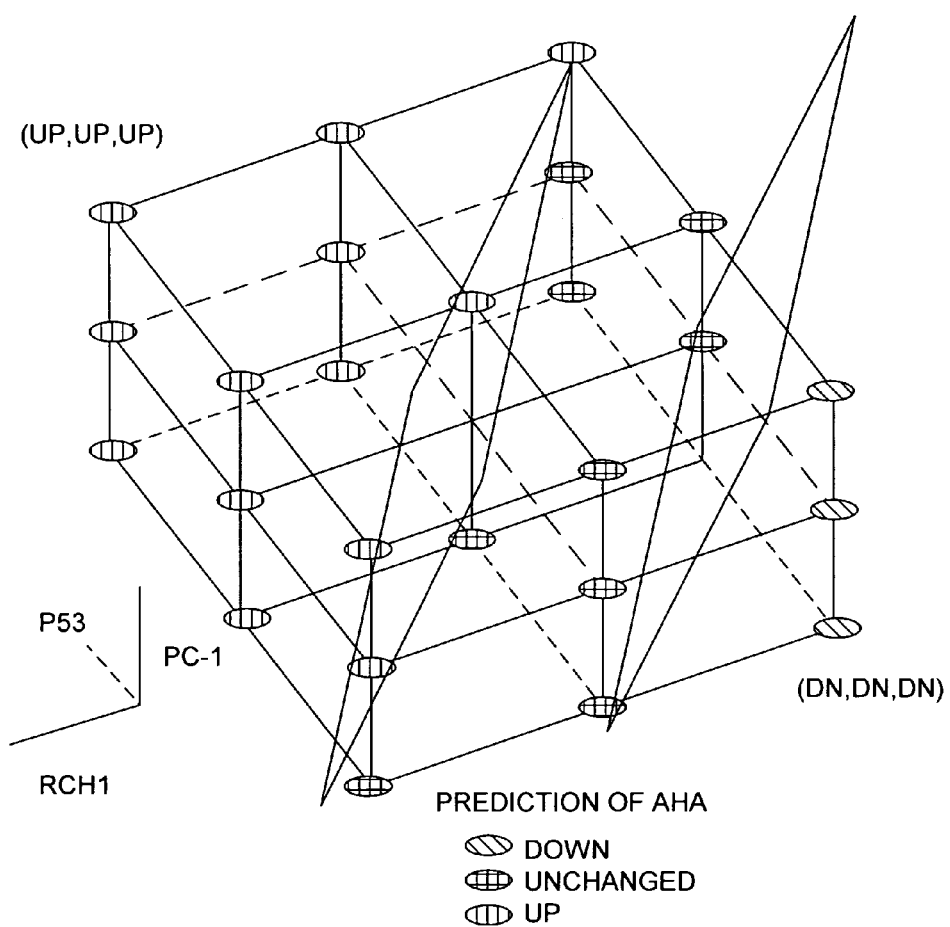
FIG. 27 is a screen capture showing a cubical representation of a perceptron for a particular set of predictive elements and a predicted gene AHA.

In addition, the perceptron predictor for a particular set of predictive elements can be displayed as a cube, with planes defining the perceptron depicted thereon. For example, FIG. 27 portrays a perceptron for predicting the gene "AHA." Although the spheres are shown in black and white in the drawing, in an implementation, values provided by the perceptron are indicated on the cube by depicting spheres of various colors. If up-regulation is predicted, a red sphere appears; if down-regulation is predicted, a green sphere appears; otherwise a yellow sphere appears.

In some cases, it may be desirable to construct a hardware circuit implementing a model. For example, in a scenario involving a large number of predictive elements and predicted genes, a set of specialized circuits could be constructed to predict gene expression via nonlinear models. Effectiveness of these circuits can be measured to quantify relatedness between the predictive elements and the predicted gene. Such an approach may be superior to a software-based approach.

Considerations concerning constraint of the models may arise due to the choice of hardware. For example, it may be particularly efficient to construct the hardware from a limited set of logic or a limited number of logic circuits. By limiting the circuit to a constrained class of hardware, a constrained logic predictor results. Thus, error relating to estimation of the coefficient of determination may be avoided.

For example, the software can generate a logical circuit implementation of the perceptron discussed above. A comparator-based logic architecture based on the signal representation theory of mathematical morphology can be used. (See Dougherty and Barrera, "Computational Gray-Scale Operators," *Nonlinear Filters for Image Processing*, pp. 61–98, Dougherty and Astola eds., SPIE and IEEE Presses, 1999.)

Figure 28:
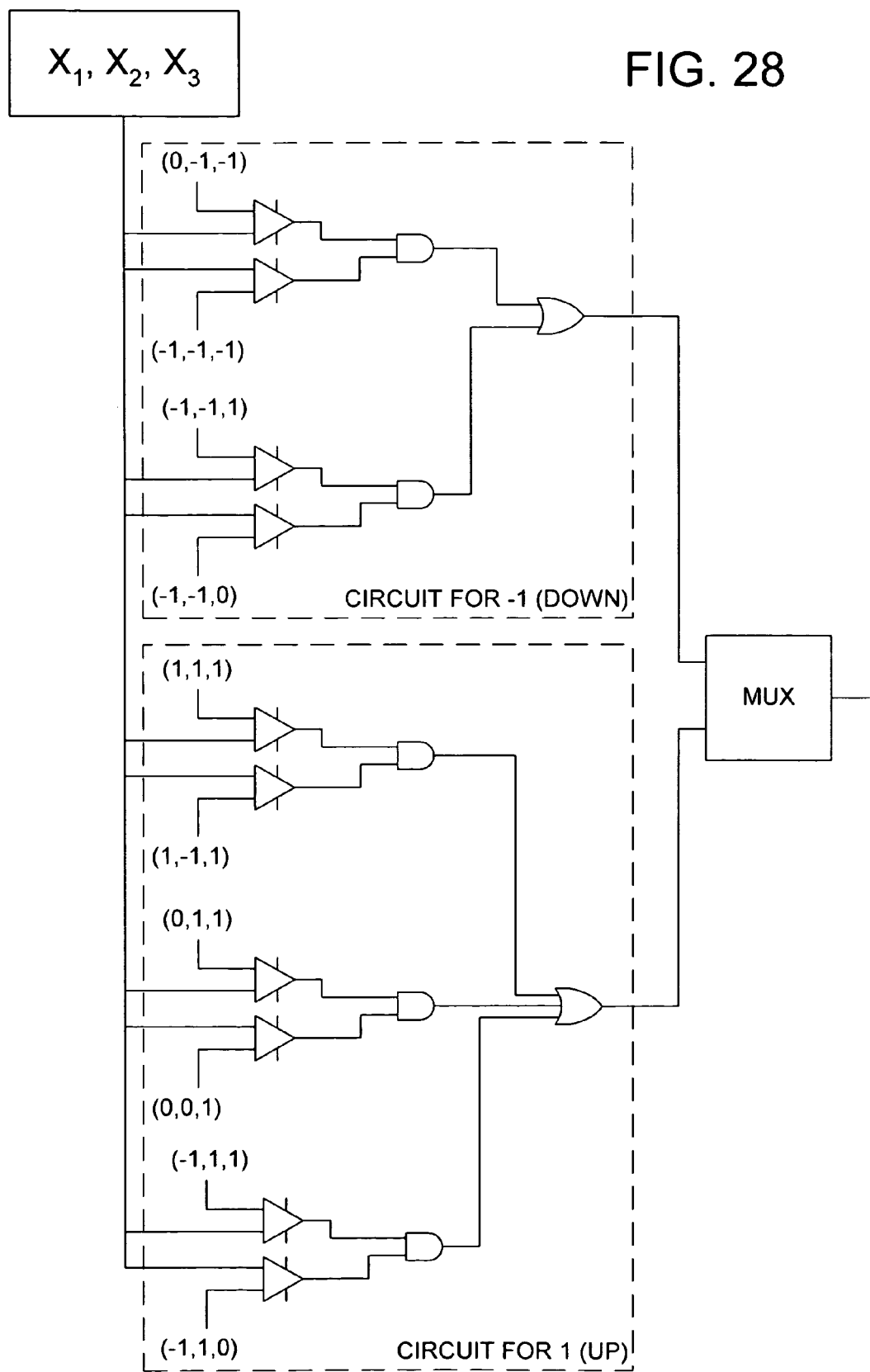
FIG. 28 is a screen capture showing a logic circuitry representation of a perceptron for a particular set of predictive elements and a predicted gene AHA.

The expression levels of the predictive elements are input in parallel to two banks of comparators, each of which is an integrated circuit of logic gates and each being denoted by a triangle having two terminals. One terminal receives the input $(x_1, x_2, x_3)$ and the other has a fixed vector input $(t_1, t_2, t_3)$. If $(t_1, t_2, t_3)$ is at the upper terminal, then the comparator outputs 1 if $x_1 \leq t_1$, $x_2 \leq t_2$ and $x_3 \leq t_3$; otherwise, it outputs 0. If $(t_1, t_2, t_3)$ is at the lower terminal, then the comparator outputs 1 if $x_1 \leq t_1$, $x_2 \geq t_2$ and $x_3 \geq t_3$; otherwise, it outputs 0. The outputs of each comparator pair enter an AND gate that outputs 1 if and only if the inputs are between the upper and lower bounds of the comparator pair. The AND outputs in the upper bank enter an OR gate, as do the AND outputs of the lower bank. The outputs of the OR gates enter a multiplexer. There are three possibilities: (1) both OR gates output 0, in which the multiplexer (and hence the circuit) outputs 0; (2) the upper OR gate outputs 1 and the lower OR gate outputs 0, in which case the multiplexer outputs −1; (3) the upper OR gate outputs 0 and the lower OR gate outputs 1, in which case the multiplexer outputs 1. FIG. 28 shows a logic implementation for the perceptron shown in FIG. 27.

A variety of other representations of a model can be used. For example, a decision tree is one way of representing the model. In some cases, there will be multiple equivalent ways to define the same model. Logic representations are useful because they sometimes result in faster analysis (e.g., when implemented in specialized hardware).

Exemplary Computer System for Conducting Analysis

FIG. 29 and the following discussion are intended to provide a brief, general description of a suitable computing environment for the computer programs described above. The method for quantifying gene relatedness is implemented in computer-executable instructions organized in program modules. The program modules include the routines, programs, objects, components, and data structures that perform the tasks and implement the data types for implementing the techniques described above.

While FIG. 29 shows a typical configuration of a desktop computer, the invention may be implemented in other computer system configurations, including multiprocessor systems, microprocessor-based or programmable consumer electronics, minicomputers, mainframe computers, and the like. The invention may also be used in distributed computing environments where tasks are performed in parallel by processing devices to enhance performance. For example, tasks related to measuring the effectiveness of a large set of nonlinear models can be performed simultaneously on multiple computers, multiple processors in a single computer, or both. In a distributed computing environment, program modules may be located in both local and remote memory storage devices.

The computer system shown in FIG. 29 is suitable for carrying out the invention and includes a computer 2920, with a processing unit 2921, a system memory 2922, and a system bus 2923 that interconnects various system components, including the system memory to the processing unit 2921. The system bus may comprise any of several types of bus structures including a memory bus or memory controller, a peripheral bus, and a local bus using a bus architecture. The system memory includes read only memory (ROM) 2924 and random access memory (RAM) 2925. A nonvolatile system 2926 (e.g., BIOS) can be stored in ROM 2924 and contains the basic routines for transferring information between elements within the personal computer 2920, such as during start-up. The personal computer 2920 can further include a hard disk drive 2927, a magnetic disk drive 2928, e.g., to read from or write to a removable disk 2929, and an optical disk drive 2930, e.g., for reading a CD-ROM disk 2931 or to read from or write to other optical media. The hard disk drive 2927, magnetic disk drive 2928, and optical disk drive 2930 are connected to the system bus 2923 by a hard disk drive interface 2932, a magnetic disk drive interface 2933, and an optical drive interface 2934, respectively. The drives and their associated computer-readable media provide nonvolatile storage of data, data structures, computer-executable instructions (including program code such as dynamic link libraries and executable files), and the like for the personal computer 2920. Although the description of computer-readable media above refers to a hard disk, a removable magnetic disk, and a CD, it can also include other types of media that are readable by a computer, such as magnetic cassettes, flash memory cards, digital video disks, and the like.

A number of program modules may be stored in the drives and RAM 2925, including an operating system 2935, one or more application programs 2936, other program modules 2937, and program data 2938. A user may enter commands and information into the personal computer 2920 through a keyboard 2940 and pointing device, such as a mouse 2942. Other input devices (not shown) may include a microphone, joystick, game pad, satellite dish, scanner, or the like. These and other input devices are often connected to the processing unit 2921 through a serial port interface 2946 that is coupled to the system bus, but may be connected by other interfaces, such as a parallel port, game port, or a universal serial bus (USB). A monitor 2947 or other type of display device is also connected to the system bus 2923 via an interface, such as a display controller or video adapter 2948. In addition to the monitor, personal computers typically include other peripheral output devices (not shown), such as speakers and printers.

The above computer system is provided merely as an example. The invention can be carried out in a wide variety of other configurations. Further, a wide variety of approaches for collecting and analyzing data related to quantifying gene relatedness is possible. For example, the data can be collected, nonlinear models built, the models' effectiveness measured, and the results presented on different computer systems as appropriate. In addition, various software aspects can be implemented in hardware, and vice versa.

Having illustrated and described the principles of the invention in exemplary embodiments, it should be apparent to those skilled in the art that the illustrative embodiments can be modified in arrangement and detail without departing from such principles. Although high throughput cDNA technology is presented as an example, any number of other art-known techniques can be used to measure gene expression, including for instance quantitative and semi-quantitative nucleotide amplification (e.g., PCR) techniques. Another approach that can be used to detect differential gene expression is a tissue microarray, as disclosed for example in PCT publications WO 99/44063 and WO 99/44062. Various other techniques are described in the following references, which are hereby incorporated herein by reference: U.S. Pat. No. 5,994,076 to Chenchik et al., entitled "Methods of assaying differential expression," filed May 21, 1997; U.S. Pat. No. 6,059,561 to Becker, entitled "Compositions and methods for detecting and quantifying biological samples," filed Jun. 9, 1998; Tewary et al., "Qualitative and quantitative measurements of oligonucleotides in gene therapy: Part I. In vitro models," *J Pharm Biomed Anal,* 15:857–73, April 1997; Tewary et al., "Qualitative and quantitative measurements of oligonucleotides in gene therapy: Part II in vivo models," *J Pharm Biomed Anal,* 15:1127–35, May 1997; Komminoth et al., "In situ polymerase chain reaction: general methodology and recent advances," *Verh Dtsch Ges Pathol,* 78:146–52, 1994; Bell et al., "The polymerase chain reaction," *Immunol Today,* 10:351–5, October 1989. Further, the principles of the invention can be applied to protein-based measurements (e.g., comparison of differential protein expression) without regard to the level of expressed nucleotides. In view of the many possible embodiments to which the principles of the invention may be applied, it should be understood that the illustrative embodiments are intended to teach these principles and are not intended to be a limitation on the scope of the invention. We therefore claim as our invention all that comes within the scope and spirit of the following claims and their equivalents.

What is claimed is:

1. A computer-implemented method for quantifying relative gene relatedness for a plurality of candidate genes for which a plurality of gene expression level observations have been collected, the method comprising:

for a predicted candidate gene selected from the plurality of candidate genes, selecting a plurality of subset gene combinations of the plurality of candidate genes, and performing (a)–(c) for each subset gene combination to generate a plurality of quantifications of relative relatedness for the predicted candidate gene and the subset combinations:

(a) based on data comprising the plurality of gene expression level observations for the plurality of candidate genes, constructing a multivariate nonlinear model predicting gene expression for the predicted candidate gene, wherein the multivariate nonlinear model accepts gene expression levels for the subset gene combination of the plurality of candidate genes as inputs and produces a gene expression level for the predicted candidate gene as an output;

(b) predicting gene expression of the predicted candidate gene with the multivariate nonlinear model; and (c) measuring effectiveness of the multivariate nonlinear model in accurately predicting the gene expression level of the predicted candidate gene as compared to the gene expression level observations, the effectiveness being a quantification of relative gene relatedness of the predicted gene and the subset gene combination of the plurality of candidate genes with respect to other subset gene combinations of the plurality of candidate genes as determined by comparing effectiveness of the multivariate nonlinear model with effectiveness of other multivariate nonlinear models constructed for other subset gene combinations, the other multivariate nonlinear models being of a same type as the multivariate nonlinear model; and presenting a ranked plurality of the plurality of quantifications of relative gene relatedness for a plurality of the subset gene combinations of the plurality of candidate genes.

2. A computer-readable medium comprising computer-readable instructions for performing the method of claim 1.

3. The method of claim 1 wherein the nonlinear model accepts a plurality of predictive elements as inputs, wherein at least one of the predictive elements indicates whether a gene expression observation is associated with having applied a particular external stimulus to biological material.

4. The method of claim 3 further comprising:

for at least one of the predictive elements, to determine contribution of the predictive element to the quantification of relatedness, constructing an additional nonlinear model predicting gene expression, wherein the additional nonlinear model has the predictive element as a single input, and measuring the effectiveness of the additional nonlinear model.

5. The method of claim 1 further comprising:

accepting by the nonlinear model a plurality of predictive elements as inputs, wherein at least one of the predictive elements indicates whether a gene expression observation is associated with a particular cell state.

6. The method of claim 1 further comprising:

accepting by the nonlinear model a plurality of predictive elements as inputs, wherein at least one of the predictive elements indicates differential gene expression between two samples of biological material.

7. The method of claim 1 wherein the nonlinear model comprises a multivariate prediction function accepting two or more inputs to predict gene expression.

8. The method of claim 1 wherein constructing the nonlinear model predicting gene expression comprises choosing a nonlinear model from a constrained set of nonlinear models.

9. The method of claim 1 wherein measuring the model's effectiveness comprises evaluating the model to estimate a coefficient of determination for an optimal model estimated by the model.

10. The method of claim 1 wherein the nonlinear model predicting gene expression is a full-logic model predicting gene expression for a predicted candidate gene, and the effectiveness of the model is measured by comparing predictions of gene expression for the predicted candidate gene by the model with observations of gene expression for the predicted candidate gene.

11. The method of claim 1 further comprising:
obtaining the plurality of gene expression level observations from results of a plurality of cDNA microarray experiments measuring mRNA transcription levels for a plurality of genes in biological material.

12. The method of claim 1 wherein the data comprising a plurality of gene expression observations is divided into a training set of data and a test set of data, wherein
the nonlinear model predicting gene expression is generated via the training set data; and
effectiveness of the nonlinear model is measured via the test set of data.

13. The method of claim 12 wherein the training set of data is extended by randomly reordering and recycling gene expression observations.

14. The method of claim 1 wherein
a plurality of training data sets are repeatedly chosen from the data comprising a plurality of gene expression observations;
the nonlinear model is one of a plurality of models constructed from the plurality of training data sets; and
quantification of the relatedness for the plurality of candidate genes is measured by measuring average effectiveness of the plurality of models constructed from the plurality of training data sets.

15. The method of claim 1 wherein the nonlinear model predicting gene expression is a truth table predicting a gene expression level for a predicted candidate gene from predictive elements comprising expression level observations for candidate genes other than the predicted candidate gene.

16. The method of claim 15 wherein the truth table comprises ternary discrete values.

17. The method of claim 15 wherein gene expression levels in the truth table are ternary discrete values.

18. The method of claim 15 wherein
the truth table comprises a plurality of rows for possible combinations of expression level observations for the candidate genes other than the predicted candidate gene; and
for at least one of the rows, the truth table indicates predicted gene expression for the predicted candidate gene with a thresholded weighted average of gene expression level observations associated with the row.

19. The method of claim 1 wherein the nonlinear model predicting gene expression is a neural network predicting gene expression.

20. The method of claim 19 wherein the neural network consists of one neuron which predicts a gene expression level for a single predicted candidate gene.

21. The method of claim 20 wherein the neuron is a ternary perceptron accepting predictive elements as inputs, wherein the predictive elements comprise gene expression levels indicated as one of three possible values: up, unchanged, and down.

22. The method of claim 21 further comprising:
displaying a three-dimensional graph representing the ternary perceptron with two planes separating points on the graph into points relating to like predicted values.

23. The method of claim 21 further comprising:
displaying a three-dimensional graph representing the ternary perceptron with objects at points in three-dimensional space within the graph, wherein axes of the graph relate to thresholded gene expression levels for three of the candidate genes.

24. The method of claim 23 wherein the objects are of a color indicating a predicted gene expression level.

25. The method of claim 23 wherein the objects are of a size indicating a number of observations related to a point on the graph.

26. The method of claim 1 wherein the data comprising a plurality of gene expression observations comprises gene expression level observations generated by subjecting sample biological material to an experimental condition and observing regulation of mRNA transcription levels for a plurality of genes in the biological material as a result of being subjected to the experimental condition.

27. The method of claim 26 wherein the data comprising a plurality of gene expression observations further comprises an indication of the experimental condition to which the biological material related to an observation was subjected and the indication is included in the model to predict gene expression.

28. The method of claim 1 wherein the gene relatedness indicates relatedness within a network controlling gene expression.

29. The method of claim 1 wherein the gene relatedness indicates relatedness based on chains of interaction among various mechanisms.

30. A computer-implemented method for identifying genes related to a target gene by analyzing gene expression level observations for the genes, the method comprising:
based on the gene expression level observations, constructing multivariate nonlinear predictors that predict an expression level for the target gene, wherein the predictors accept gene expression levels for other genes as predictive elements;
estimating a coefficient of determination for sets of predictive elements and the target gene by comparing results of the multivariate nonlinear predictors with gene expression level observations for the target gene, wherein the predictive elements comprise expression level observations for groups of genes other than the target gene; and
ranking the groups of genes other than the target gene by coefficient of determination to present the groups of genes other than the target gene in order of likelihood of relatedness to the target gene.

31. The method of claim 30 further comprising:
indicating a proper subset of the genes having the highest likelihood of relatedness to the target gene.

32. A computer-implemented method for analyzing gene expression level observations for a set of genes comprising a target gene, the method comprising:
estimating a coefficient of determination for an optimal multivariate nonlinear model predicting gene expression of the target gene by constructing a multivariate nonlinear model from the gene expression level observations of gene expression for the target gene, wherein the optimal multivariate nonlinear model and the constructed multivariate nonlinear model predict gene expression of the target gene based on variables representing gene expression levels of genes other than the target gene.

33. The method of claim 32 wherein the optimal multivariate nonlinear model and the constructed multivariate nonlinear model predict gene expression based, at least in part, on inputs comprising an indication of a condition to which biological material relating to the observations has been subjected.

34. A method for identifying related genes out of a set of genes for which gene expression level observations have been collected, the method comprising:
   for at least one predicted gene out of the set of genes, training an artificial intelligence function to predict gene expression for the predicted gene, wherein the artificial intelligence function takes one or more predictive elements as inputs and produces a gene expression level for the predicted gene as an output, wherein at least one of the predictive elements is a gene expression level for a gene other than the predicted gene;
   testing effectiveness of the artificial intelligence function in predicting expression of the predicted gene to rate relative relatedness of the predicted gene and at least one gene associated with the predictive elements; and
   presenting the relative relatedness in a computer user interface showing a ranking of relative relatedness for a plurality of gene groups.

35. The method of claim 34 wherein the artificial intelligence function takes a plurality of predictive elements as inputs.

36. The method of claim 34 wherein the predictive elements comprise a variable indicating biological material was subjected to an experimental condition.

37. For a plurality of observed genes for which expression levels have been observed, a method of presenting an analysis of the expression levels to assist in identifying related genes, the method comprising:
   denoting a particular observed gene as a predicted gene;
   for the predicted gene, constructing a plurality of nonlinear multivariate models predicting expression of the observed gene, wherein the nonlinear multivariate models comprise a variety of predictive elements chosen from permutations of expression levels of observed genes other than the predicted gene;
   measuring effectiveness of the nonlinear multivariate models in predicting expression of the predicted gene to quantify relatedness between the predicted gene and the set of genes associated with the predictive elements of the models; and
   presenting a quantification of relatedness between the predicted gene and a set of genes associated with the predictive elements of at least one of the models.

38. The method of claim 37 further comprising:
   for a set of predictive elements and a predicted gene, displaying a graph indicating the amount of increase in the effectiveness of the model for each of the predictive elements.

39. The method of claim 37 wherein at least two of the plurality of nonlinear multivariate models predicting expression of the observed gene are implemented in specialized hardware circuits for predicting gene expression.

40. The method of claim 37 further comprising:
   displaying a user interface for evaluating the analysis, wherein the user interface comprises display elements graphically indicating the relatedness of the predicted gene to a plurality of gene sets.

41. The method of claim 40 further comprising:
   displaying only those display elements indicating sets of genes in which each gene in the set improves the relatedness.

42. The method of claim 40 further comprising:
   accepting as input a set of one or more designated predictor genes;
   accepting as input a threshold relatedness;
   accepting as input a set of one or more designated predicted genes; and
   limiting the display elements of the user interface to those sets of genes having as members the one or more designated predictor genes and having at least the threshold relatedness for the one or more designated predicted genes.

43. The method of claim 40 further comprising:
   accepting as input a set of one or more designated predictor genes; and
   limiting display elements of the user interface to those sets of genes having the one or more designated predictor genes.

44. The method of claim 43 further comprising:
   accepting as input a threshold increase in relatedness; and
   further limiting display elements of the user interface to those sets of genes for which addition of the one or more designated predictor genes increases the relatedness by at least the threshold increase in relatedness.

45. The method of claim 37 further comprising presenting a ranking of gene sets according to their relatedness, wherein the ranking indicates which genes are in the sets.

46. The method of claim 45 wherein the ranking further indicates contribution of individual predictive elements to the effectiveness of the models.

47. The method of claim 37 wherein the predictive elements comprise a variable indicative of whether biological material related to a gene expression observation has been subjected to a particular condition.

48. For a plurality of observed genes for which expression levels have been observed, a method of performing an analysis of the expression levels to assist in identifying related genes, the method comprising:
   (a) for a plurality of the observed genes, denoting a particular observed gene as a predicted gene and performing at least (b) and (c);
   (b) for the predicted gene, constructing a plurality of nonlinear multivariate models predicting expression of the predicted gene, wherein the nonlinear multivariate models have a variety of predictive elements chosen from permutations of expression levels of observed genes other than the predicted gene;
   (c) measuring effectiveness of the nonlinear multivariate models in predicting expression of the predicted gene to provide a quantification of relative relatedness between the predicted gene and genes associated with the predictive elements of the models.

49. The method of claim 48 further comprising:
   skipping designating genes having fewer than a defined number of changes in expression level as predicted genes.

50. The method of claim 48 further comprising:
   displaying a user interface comprising display elements indicating gene relatedness for a plurality of genes associated with the predictive elements for a plurality of predicted genes.

51. A system for quantifying gene relatedness for a plurality of candidate genes for which a plurality of gene expression level observations have been collected, the system comprising:
- means for constructing a nonbinary, nonlinear model predicting gene expression based on data comprising the plurality of gene expression level observations for the plurality of candidate genes;
- means for predicting gene expression with the nonbinary, nonlinear model; and
- means for measuring effectiveness of the nonbinary, nonlinear model in predicting gene expression, the effectiveness indicating gene relatedness for the plurality of candidate genes.

52. The system of claim 51 wherein the means for predicting gene expression is selected from the croup consisting of: a specialized hardware circuit, a decision tree, and a truth table chosen from a constrained set of truth tables.

53. A computer-implemented method of ranking the relatedness of a plurality of genes based on gene expression level observations associated with the plurality of genes, the method comprising:
- based on the gene expression level observations, constructing a plurality of multivariate nonlinear predictors to predict the expression of a plurality of target genes out of the genes, wherein the multivariate nonlinear predictors comprise predictive elements comprising an observed gene, thereby associating the multivariate nonlinear predictor with the target gene and at least one observed gene;
- testing effectiveness of the plurality of multivariate nonlinear predictors in predicting gene expression to quantify relative gene relatedness between the genes associated with the predictors by estimating a coefficient of determination; and
- displaying a ranked list of relative gene relatedness among the genes as determined by testing the plurality of multivariate nonlinear predictors.

54. A computer-implemented method for analyzing a plurality of candidate genes for which a plurality of gene expression level observations have been collected to determine which out of the genes are more related, the method comprising:
- for a plurality of selected permutations of the plurality of candidate genes, performing
- (a)–(c) for each permutation:
- (a) based on data comprising the plurality of gene expression level observations for the plurality of candidate genes, constructing a nonlinear model predicting gene expression for the permutation of the plurality of candidate genes;
- (b) predicting gene expression with the nonlinear model; and
- (c) measuring effectiveness of the nonlinear model in predicting gene expression, the effectiveness being a quantification indicating relative gene relatedness for the plurality of candidate genes of the permutation; and
- presenting at least one of the permutations of genes as related and an indication of the quantification indicating relative gene relatedness for the at least one of the permutations.

55. The method of claim 54 wherein the gene relatedness indicates relatedness within a network controlling gene expression.

56. A computer-implemented method comprising:
- constructing a first multivariate nonlinear model for predicting a gene expression level for a candidate gene selected out of an observed set of genes, wherein the gene expression level for the candidate gene is predicted by the first multivariate nonlinear model via observed gene expression levels for a first permutation subset of genes selected out of the observed set of genes, the first nonlinear model taking observed gene expression levels for the first permutation subset of genes as inputs;
- measuring effectiveness of the first multivariate nonlinear model in predicting the observed gene expression level of the candidate gene;
- constructing a second multivariate nonlinear model for predicting the gene expression level for the candidate gene selected out of the observed set of genes, wherein the gene expression level for the candidate gene is predicted by the second multivariate nonlinear model via observed gene expression levels for a second permutation subset of genes selected out of the observed set of genes, the second nonlinear model taking observed gene expression levels for the second permutation subset of genes as inputs, wherein the first multivariate nonlinear model and the second multivariate nonlinear model are of a same model type, wherein the first multivariate nonlinear model and the second multivariate nonlinear model predict the gene expression level for the candidate gene, and wherein the first multivariate nonlinear model and the second multivariate nonlinear model are constructed via gene expression data from a same set of experiments;
- measuring effectiveness of the second multivariate nonlinear model in predicting the observed gene expression level of the candidate gene;
- ordering the first and second multivariate nonlinear models by ranking the effectiveness of the first multivariate nonlinear model with respect to the effectiveness of the second multivariate nonlinear model; and
- presenting results of the ordering, wherein the results indicate that observed gene expression levels for a permutation subset of genes associated with a higher-ranking multivariate nonlinear model have a higher effectiveness in predicting the observed gene expression level of the candidate gene than those of observed gene expression levels for a permutation subset of genes associated with a lower-ranking multivariate nonlinear model.

57. The method of claim 56, wherein the higher-ranking multivariate nonlinear model having the higher effectiveness of the two models is presented as indicating a higher relatedness between the genes that comprise the permutation subset and the candidate gene of the higher-ranking multivariate nonlinear model relative to relatedness between the genes that comprise the permutation subset and the candidate gene of the lower-ranking multivariate nonlinear model.

58. The method of claim 56, further comprising:
- with additional permutation subsets, constructing additional multivariate nonlinear models predicting expression levels for a gene other than the candidate gene;
- measuring effectiveness for the additional multivariate nonlinear models; and
- including results for the additional multivariate nonlinear models in the presenting.

59. The method of claim 56, wherein the model type is a neural network.

60. The method of claim 59, wherein the neural network consists of one neuron which predicts a gene expression level for the candidate gene.

61. The method of claim 60 wherein the neuron is a ternary perceptron accepting gene expression levels as input, and wherein the gene expression levels are indicated as one of three possible values: up, unchanged, and down.

62. The method of claim 61 further comprising:
displaying a three-dimensional graph representing the ternary perceptron with two planes separating points on the graph into points relating to like predicted values.

63. The method of claim 61 further comprising:
displaying a three-dimensional graph representing the ternary perceptron with objects at points in three-dimensional space within the graph, wherein axes of the graph relate to thresholded gene expression levels for three of the candidate genes.

64. The method of claim 63 wherein the objects are of a color indicating a predicted gene expression level.

65. The method of claim 56 wherein the objects are of a size indicating a number of observations related to a point on the graph.

66. The method of claim 56, wherein the first permutation subset of the genes is a proper subset of the second permutation subset of the genes.

67. The method of claim 56, wherein measuring effectiveness of a multivariate nonlinear model comprises evaluating the multivariate nonlinear model to determine a coefficient of determination that represents ability of the model to accurately predict the gene expression level of the candidate gene.

68. A computer-readable medium comprising computer-readable instructions for performing the method of claim 56.

69. The computer-implemented method of claim 56, further comprising:
constructing one or more additional multivariate nonlinear models for predicting the gene expression level for the candidate gene selected out of the observed set of genes, wherein the gene expression level for the candidate gene is predicted via observed gene expression levels for additional permutation subsets of genes selected out of the observed set of genes, and wherein the first, second, and the one or more additional multivariate nonlinear models are of the same model type and constructed from same training data;
measuring effectiveness of the one or more additional multivariate nonlinear models in predicting the observed gene expression level of the candidate gene;
in the ordering, including the one or more additional multivariate nonlinear models with the first and second multivariate nonlinear models; and
in the presenting, including the one or more additional multivariate nonlinear models with the first and second multivariate nonlinear models.

70. The method of claim 69, wherein the one or more additional multivariate nonlinear models predict the gene expression level of the candidate gene by further including at least one predictive element with the additional permutation subsets of genes.

71. The method of claim 70, further comprising:
to determine contribution of a predictive element or individual gene to the prediction of the expression level of the candidate gene, constructing an additional nonlinear model of a same model type using a same training set, wherein the additional nonlinear model has the predictive element or individual gene as a single predictor, and measuring the effectiveness of the additional nonlinear model.

72. The method of claim 70, wherein the at least one predictive element indicates whether a gene expression observation is associated with having applied a particular external stimulus to biological material.

73. The method of claim 70, wherein the at least one predictive element indicates whether a gene expression observation is associated with a particular cell state.

74. The method of claim 70, wherein the at least one predictive element indicates differential gene expression between two samples of biological material.

75. The method of claim 56, wherein the model type is a full-logic model.

76. The computer-implemented method of claim 56, wherein the genes that comprise the permutation subset in the higher-ranking multivariate nonlinear model exhibit more predictive power in predicting the observed gene expression of the candidate gene than the genes that comprise the permutation subset in the lower-ranking multivariate nonlinear model.

77. The method of claim 56, wherein the observed gene expression levels for the observed set of genes are obtained from results of a plurality of cDNA microarray experiments measuring mRNA transcription levels for a plurality of genes in biological material.

78. The method of claim 56 wherein data comprising a plurality of gene expression observations is divided into a training set of data and a test set of data, wherein
the first and second multivariate nonlinear models are constructed via the training set data; and
effectiveness of the first and second multivariate nonlinear models are measured via the test set of data.

79. The method of claim 78, wherein the training set of data is extended by randomly reordering and recycling gene expression observations.

80. The method of claim 56 wherein the observed gene expression levels for the observed set of genes comprise gene expression level observations generated by subjecting sample biological material to an experimental condition and observing regulation of mRNA transcription levels for a plurality of genes in the biological material as a result of being subjected to the experimental condition.

81. The method of claim 80 wherein the observed gene expression levels for the observed set of genes further comprise an indication of the experimental condition to which the biological material related to an observation was subjected and the indication is included in the first and second multivariate nonlinear models to predict gene expression of the candidate gene.

* * * * *

UNITED STATES PATENT AND TRADEMARK OFFICE
CERTIFICATE OF CORRECTION

| | |
|---|---|
| PATENT NO. | : 7,003,403 B1 |
| APPLICATION NO. | : 09/595580 |
| DATED | : February 21, 2006 |
| INVENTOR(S) | : Dougherty et al. |

It is certified that error appears in the above-identified patent and that said Letters Patent is hereby corrected as shown below:

Title Page
Item [54], Title, "QUANTIFYING GENE RELATEDNESS VIA NONLINEAR PREDICTION OF GENE" should read --QUANTIFYING GENE RELATEDNESS VIA NONLINEAR PREDICTION OF GENE EXPRESSION LEVELS--.

Item [75], Inventors, the following inventor has been omitted from the printed patent: --Krishnamoorthy Sivakumar, Pullman, WA (India)--.

Column 10
Lines 17-18, in TABLE 3, " ⋯ " should be listed below the column header "$Y_{pred}$".
  $y_{27}$ Column 11
Line 39, "presented" should read --presented.--.
Line 43, "150c" should read --1150*c*--

Column 16
Line 21, "$\epsilon_{con.n}$" should read --$\epsilon_{con,n}$--.
Line 24, "[$\epsilon_{con.n}$]" should read --[$\epsilon_{con,n}$]--.
Line 25, "$\delta_{con.n}$" should read -- $\delta_{con,n}$--.
Line 25, "[$\epsilon_{con.n}$]" should read --[$\epsilon_{con,n}$]--.
Line 28, "$\delta_{con.n}$" should read -- $\delta_{con,n}$--.
Line 30, "$\delta_{con.n}$" should read -- $\delta_{con,n}$--.
Line 32, "$\delta_{con.n}$" should read -- $\delta_{con,n}$--.
Line 36, "$\delta_{con.n}$" should read -- $\delta_{con,n}$--.
Line 38, "$\approx\epsilon_{con.n}$" should read --$\approx\epsilon_{con,n}$--.
Line 41, "$\delta_{con.n}$" should read --$\delta_{con,n}$--.
Line 49, "E[$\epsilon_{con.n}$]" should read --E[$\epsilon_{con,n}$]--.
Line 50, "E[$\epsilon_{con.n}$]" should read --E[$\epsilon_{con,n}$]--.
Line 50, "$N_2$" should read -- $N_1$--.
Line 51, "E[$\epsilon_{con.n}$]" should read --E[$\epsilon_{con,n}$]--.

Column 17
Line 37, "E[$\epsilon_n$]<$\theta_{opt}$" should read --yield E[$\theta_n$]<$\theta_{opt}$--.
Line 39, "$\epsilon_{con.n}$" should read -- $\epsilon_{con,n}$--.
Line 40 "$\epsilon_{con.n}$" should read --$\theta_{con,n}$--
Line 46, "[$\theta_{con.n}$]" should read --[$\theta_{con,n}$]--.

UNITED STATES PATENT AND TRADEMARK OFFICE
CERTIFICATE OF CORRECTION

PATENT NO. : 7,003,403 B1
APPLICATION NO. : 09/595580
DATED : February 21, 2006
INVENTOR(S) : Dougherty et al.

It is certified that error appears in the above-identified patent and that said Letters Patent is hereby corrected as shown below:

Column 21
"TABLE 4-continued", at row 20 K562, "0 0 0 0-1 0 0 0 1 0" should read
--0 0 0 0 -1 0 0 1 0 0--.
Line 55, "PC 1" should read --PC1--.

Column 25
Lines 14-15, the following paragraph was omitted from the printed patent: --A set of two planes defines the perceptron and will separate the groups of colored spheres into three regions, where each region contains spheres of the same color. The display can be rotated.--

Column 35
In Claim 65, Line 17, "claim 56" should read --claim 63--.

Signed and Sealed this

Fifth Day of December, 2006

JON W. DUDAS
*Director of the United States Patent and Trademark Office*